US007851192B2

(12) United States Patent
Guan et al.

(10) Patent No.: US 7,851,192 B2
(45) Date of Patent: Dec. 14, 2010

(54) MODIFIED DNA CLEAVAGE ENZYMES AND METHODS FOR USE

(75) Inventors: Chudi Guan, Wenham, MA (US); Sanjay Kumar, Ipswich, MA (US); Rebecca Kucera, Hamilton, MA (US)

(73) Assignee: New England Biolabs, Inc., Ipswich, MA (US)

( * ) Notice: Subject to any disclaimer, the term of this patent is extended or adjusted under 35 U.S.C. 154(b) by 684 days.

(21) Appl. No.: 10/585,964

(22) PCT Filed: Nov. 22, 2004

(86) PCT No.: PCT/US2004/039288

§ 371 (c)(1), (2), (4) Date: Jul. 13, 2006

(87) PCT Pub. No.: WO2005/052124

PCT Pub. Date: Jun. 9, 2005

(65) Prior Publication Data

US 2007/0042379 A1 Feb. 22, 2007

(51) Int. Cl.

| | |
|---|---|
| ***C12N 9/16*** | (2006.01) |
| ***C12Q 1/44*** | (2006.01) |
| ***C12Q 1/68*** | (2006.01) |
| ***C07K 14/00*** | (2006.01) |
| *C12N 15/00* | (2006.01) |
| *C12N 1/21* | (2006.01) |
| *C12P 21/00* | (2006.01) |
| *C07H 21/00* | (2006.01) |

(52) U.S. Cl. ............................ 435/196; 435/6; 435/19; 435/69.1; 435/320.1; 435/252.3; 530/350; 536/23.2

(58) Field of Classification Search ................. 435/196, 435/69.1, 320.1, 252.3, 325, 19; 530/350; 536/23.2

See application file for complete search history.

(56) References Cited

U.S. PATENT DOCUMENTS 5,604,098 A 2/1997 Mead et al.
6,340,566 B1 1/2002 McCutchen-Maloney

OTHER PUBLICATIONS

Branden et al., Introduction to Protein Structure, Garland Publishing Inc., New York, p. 247, 1991.*

Witkowski et al., Biochemistry 38:11643-11650, 1999.*

Seffernick et al., J. Bacteriol. 183(8):2405-2410, 2001.*

Beck et al., UniProt accession No. P20314, Feb. 1, 1991.*

Aravind, et al., "Holliday junction resolvases and related nucleases: identification of new families, phletic distribution and evolutionary trajectories," *Nucleic Acids Research* 28(18): 3417-3432 (2000).

Déclais, et al., "The complex between a four-way DNA junction and T7 endonuclease I," *EMBO J.* 22:1398-1409 (2003).

Duckett, et al., "Binding of the Junction-resolving Enzyme Bacteriophage T7 Endonuclease I to DNA: Separation of Binding and Catalysis by Mutation," *J. Mol. Biol.* 246:95-107 (1995).

Geer, et al., "CDART: Protein Homology by Domain Architecture," *Genome Research* 12:1619-1623 (2002).

Guan, et al., "Changing the Enzymatic Activity of T7 Endonuclease by Mutations at the β-Bridge Site: Alteration of Substrate Specificity Profile and Metal Ion Requirements by Mutation Distant from the Catalytic Domain," *Biochemistry* 43:4313-4322 (2004).

Guan, et al., "Activation of Glycosylasparaginase," *J. Biol. Chem.* 19:1732-1737 (1996).

Hadden et al., "Crystal structure of the Holliday junction resolving enzyme T7 endonuclease I," *Nature Structural Biology* 8(1): 62-67 (2001).

Lilley, D.M.J., "All change at Holliday junction," *PNAS* 94, 9513-9515 (1997).

Mashal, et al., "Detection of mutations by cleavage of DNA heteroduplexes with bacteriophage resolvases," *Nat. Genet.* 9:177-183 (1995).

Parkinson, et al., "The Junction-resolving Enzyme T7 Endonuclease I: Quaternary Structure and Interaction with DNA," *J. Mol. Biol.* 270:169-178 (1997).

White, et al., "Recognition and Manipulation of Branched DNA Structure by Junction-resolving Enzymes," *J. Mol. Biol.* 269:647-664 (1997).

Database UniProt Feb. 1, 1991 "Endodeoxyribonuclease 1 (EC 3.1.21.2)(Endodeoxyribonuclease I) (Endonuclease)." retrieved from EBI accession No. UNIPROT:P20314.

Database Uniprot May 1, 2000 "Endonuclease." retrieved from EBI accession No. UNIPROT: Q9T133.

Database Uniprot Jun. 1, 2003 "Endonuclease." retrieved from EBI accession No. UNIPROT:Q858M4.

Dunderdale, H.J., et al., *Journal of Biological Chemistry*, 269(7): 5187-5194 (1994).

Fitzgerald, M.C. et al., *Nucleic Acids Research*, 20(14): 3753-3762 (1992).

Llosa, et al., *Journal of Molecular Biology*, 246(1): 54-62 (1995).

Whitby, M.C., et al., *Journal of Molecula r Biology*, 272(4): 509-522 (1997).

* cited by examiner

*Primary Examiner*—Delia M Ramirez
(74) *Attorney, Agent, or Firm*—Harriet M. Strimpel

(57) ABSTRACT

Compositions and methods are provided that relate to a modified DNA cleaving enzyme having at least 35% amino acid sequence identity with T7 Endo I. The modified enzyme includes two catalytic centers separated by a β-bridge where the β-bridge contains at least one mutation having an effect of altering enzyme cleavage activity compared to the unmodified enzyme. Activities associated with the modified DNA cleaving enzyme that can be modulated in different reaction conditions include at least one of: (a) non-sequence specific nicking activity; (b) cleaving the second strand of a duplex DNA at a preexisting nick site to produce a linear duplex with a single strand overhang; (c) non-sequence specific DNA cleavage; (d) cleaving DNA flanking a mismatch; and (e) cleavage at a cruciform structure in a DNA duplex.

11 Claims, 22 Drawing Sheets

Figure 9
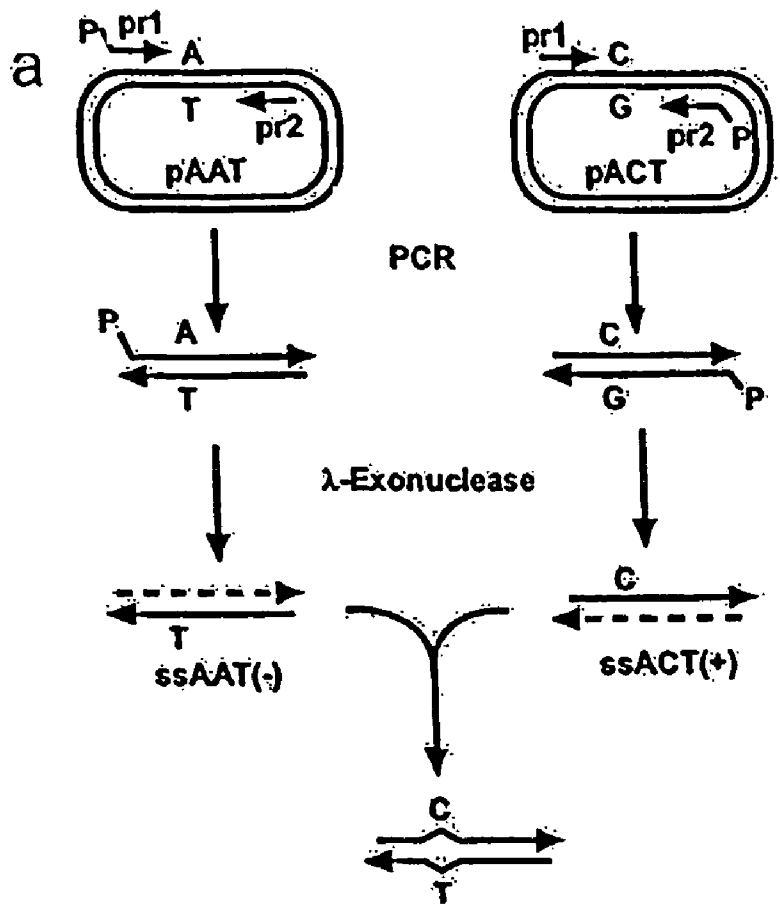
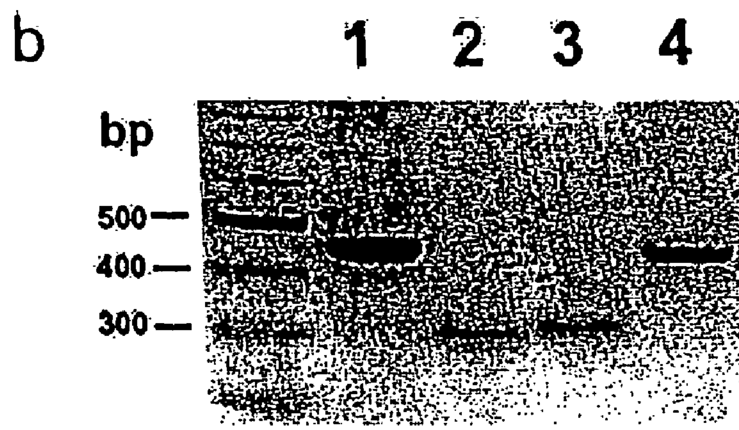

Figure 10
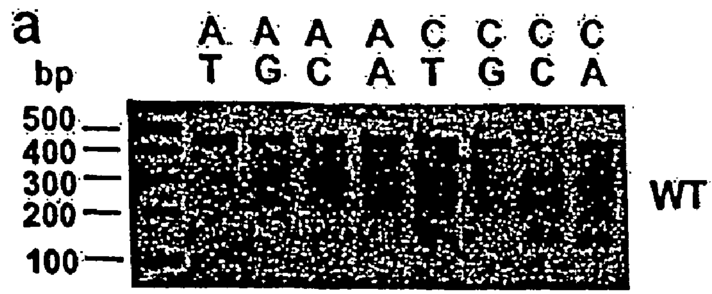
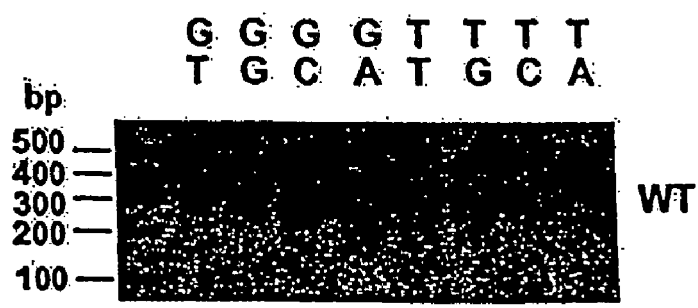
b
A A A A C C C C
T G C A T G C A
bp
500
300
100
PA/A
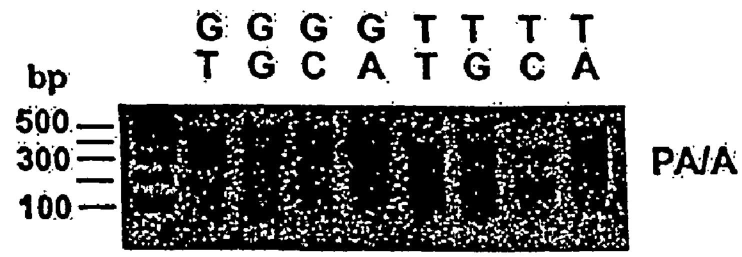

Figure 13

T7_endo1

>gi|431187:10257-10706 gene 3, endonuclease
ATGGCAGGTTACGGCGCTAAAGGAATCCGAAAGGTTGGAGCGTTTCGCTCTGGCC
TAGAGGACAAGGTTTCAAAGCAGTTGGAATCAAAAGGTATTAAATTCGAGTATGAA
GAGTGGAAAGTGCCTTATGTAATTCCGGCGAGCAATCACACTTACACTCCAGACTT
CTTACTTCCAAACGGTATATTCGTTGAGACAAAGGGTCTGTGGGAAAGCGATGATA
GAAAGAAGCACTTATTAATTAGGGAGCAGCACCCCGAGCTAGACATCCGTATTGTC
TTCTCAAGCTCACGTACTAAGTTATACAAAGGTTCTCCAACGTCTTATGGAGAGTTC
TGCGAAAAGCATGGTATTAAGTTCGCTGATAAACTGATACCTGCTGAGTGGATAAA
GGAACCCAAGAAGGAGGTCCCCTTTGATAGATTAAAAAGGAAAGGAGGAAAGAAA
TAA (SEQ ID NO:1)

>gi|15581|emb|CAA24402.1| unnamed protein product [Enterobacteria phage T7]
MAGYGAKGIRKVGAFRSGLEDKVSKQLESKGIKFEYEEWKVPYVIPASNHTYTPDFL
LPNGIFVETKGLWESDDRKKHLLIREQHPELDIRIVFSSSRTKLYKGSPTSYGEFCEK
HGIKFADKLIPAEWIKEPKKEVPFDRLKRKGGKK (SEQ ID NO:12)

Figure 14-1

>gi|37956656|gb|AAP33926.1| gene 3 [Enterobacteria phage T7]
MAGYGAKGIRKVGAFRSGLEDKVSKQLESKGIKFEYEEWKVPYVIPASNHTYT
PDFLLPNGIFVETKGLWESDDRKKHLLIREQHPELDIRIVFSSSRTKLYKGSPTS
YGEFCEKHGIKFADKLIPAEWIKEPKKEVPFDRLKRKGGKK (SEQ ID NO:12)

>gi|9627444|ref|NP_041972.1| endonuclease [Enterobacteria phage T7]
MAGYGAKGIRKVGAFRSGLEDKVSKQLESKGIKFEYEEWKVPYVIPASNHTYT
PDFLLPNGIFVETKGLWESDDRKKHLLIREQHPELDIRIVFSSSRTKLYKGSPTS
YGEFCEKHGIKFADKLIPAEWIKEPKKEVPFDRLKRKGGKK (SEQ ID NO:12)

>gi|119370|sp|P00641|ENRN_BPT7 Endodeoxyribonuclease I (Endonuclease)
MAGYGAKGIRKVGAFRSGLEDKVSKQLESKGIKFEYEEWKVPYVIPASNHTYT
PDFLLPNGIFVETKGLWESDDRKKHLLIREQHPELDIRIVFSSSRTKLYKGSPTS
YGEFCEKHGIKFADKLIPAEWIKEPKKEVPFDRLKRKGGKK (SEQ ID NO:12)

>gi|67296|pir||NEBP37 endodeoxyribonuclease I (EC 3.1.21.-) - phage T7
MAGYGAKGIRKVGAFRSGLEDKVSKQLESKGIKFEYEEWKVPYVIPASNHTYT
PDFLLPNGIFVETKGLWESDDRKKHLLIREQHPELDIRIVFSSSRTKLYKGSPTS
YGEFCEKHGIKFADKLIPAEWIKEPKKEVPFDRLKRKGGKK (SEQ ID NO:12)

Figure 14-2

>gi|15517|emb|CAA24345.1| unnamed protein product [Enterobacteria phage T7]
MAGYGAKGIRKVGAFRSGLEDKVSKQLESKGIKFEYEEWKVPYVIPASNHTYT
PDFLLPNGIFVETKGLWESDDRKKHLLIREQHPELDIRIVFSSSRTKLYKGSPTS
YGEFCEKHGIKFADKLIPAEWIKEPKKEVPFDRLKRKGGKK (SEQ ID NO:12)

===============

>gi|37956869|gb|AAP34135.1| gene 3 [Enterobacteria phage T7]
MAGYSAKGIRKVGAFRSGLEDKVSKQLESKGIKFEYEEWKVPYVIPASNHTYT
PDFLLPNGIFVETKGLWESDDRKKHLLIRKQHPELDIRIVFSSSRTKLYKGSPTS
YGEFCEKHGIKFADKLIPAEWIKEPKKEVPFDRLKRKGGKK (SEQ ID NO:22)

>gi|37956815|gb|AAP34082.1| gene 3 [Enterobacteria phage T7]
MAGYSAKGIRKVGAFRSGLEDKVSKQLESKGIKFEYEEWKVPYVIPASNHTYT
PDFLLPNGIFVETKGLWESDDRKKHLLIRKQHPELDIRIVFSSSRTKLYKGSPTS
YGEFCEKHGIKFADKLIPAEWIKEPKKEVPFDRLKRKGGKK (SEQ ID NO:22)

==========

>gi|37956764|gb|AAP34032.1| gene 3 [Enterobacteria phage T7]
MVGYGVKGIRKVGAFRSGLEDKVSKQLESKGIKFEYEEWKVPYVIPASNHTYT
PDFLLPNGIFVETKGLWESDDRKKHLLIREQHPELDIRIVFSSSRTKLYKGSPTS
YGEFCEKHGIKFADKLIPAEWIKEPKKEVSFDRLKRKGGKK (SEQ ID NO:23)

Figure 14-3

>gi|37956712|gb|AAP33981.1| gene 3 [Enterobacteria phage T7]
MVGYGVKGIRKVGAFRSGLEDKVSKQLESKGIKFEYEEWKVPYVIPASNHTYT
PDFLLPNGIFVETKGLWESDDRKKHLLIREQHPELDIRIVFSSSRTKLYKGSPTS
YGEFCEKHGIKFADKLIPAEWIKEPKKEVSFDRLKRKGGKK (SEQ ID NO:23)

==========

>gi|30387466|ref|NP_848275.1| endonuclease [Yersinia pestis phage phiA1122]
MAGTYAARGIRKVGTFRSGLEDKVSKQLEGKGIKFDYELWKIPYVVPASNHVY
TPDFLLPNGIFIETKGLWESDDRKKHLLIREQFPELDIRLVFSSSRTKLYKGSPT
SYGEWCEKHGILFADKLIPVEWLKEPKKEVPFDRLKQAKGGKK
(SEQ ID NO:13)

>gi|30314103|gb|AAP20511.1| endonuclease [Yersinia pestis phage phiA1122]
MAGTYAARGIRKVGTFRSGLEDKVSKQLEGKGIKFDYELWKIPYVVPASNHVY
TPDFLLPNGIFIETKGLWESDDRKKHLLIREQFPELDIRLVFSSSRTKLYKGSPT
SYGEWCEKHGILFADKLIPVEWLKEPKKEVPFDRLKQAKGGKK
(SEQ ID NO:13)

>gi|9634009|ref|NP_052083.1| endonuclease [Bacteriophage phiYeO3-12]
MAGAYAARGVRKVGAFRSGLEDKVSKQLESKGIKFDYELWRIPYVIPASDHLY
TPDFLLPNGIFIETKGLWDSDDRKKHLLIREQHPELDIRLVFSSSRSKLYKGSPT
SYAEWCEKHGILFADKLIPVEWLKEPKKEVPFDKFKTKKGVKKNG
(SEQ ID NO:14)

>gi|6599000|emb|CAB63604.1| endonuclease [Bacteriophage phiYeO3-12]
MAGAYAARGVRKVGAFRSGLEDKVSKQLESKGIKFDYELWRIPYVIPASDHLY
TPDFLLPNGIFIETKGLWDSDDRKKHLLIREQHPELDIRLVFSSSRSKLYKGSPT
SYAEWCEKHGILFADKLIPVEWLKEPKKEVPFDKFKTKKGVKKNG
(SEQ ID NO:14)

===========

>gi|17570803|ref|NP_523312.1| endonuclease [Bacteriophage T3]
MAGAYAARCTQGRAFRSGLEDKVSKQLESKGIKFDYELWRIPYVIPESDHLYT
PDFLLPNGIFIETKGLWDSDDRKKHLLIREQHPELDIRLVFSSSRSKLYKGSPTS
YGEWCEKHGILFADKLIPVAGVKEPKKEVPFDKFKTKKGVKKNG
(SEQ ID NO:15)

>gi|17384287|emb|CAC86275.1| endonuclease [Bacteriophage T3]
MAGAYAARCTQGRAFRSGLEDKVSKQLESKGIKFDYELWRIPYVIPESDHLYT
PDFLLPNGIFIETKGLWDSDDRKKHLLIREQHPELDIRLVFSSSRSKLYKGSPTS
YGEWCEKHGILFADKLIPVAGVKEPKKEVPFDKFKTKKGVKKNG
(SEQ ID NO:15)

Figure 14-5

>gi|119369|sp|P203|ENRN_BPT3 ENDODEOXYRIBONUCLEASE I (ENDONUCLEASE)
MAGAYAARCTQGRAFRSGLEDKVSKQLESKGIKFDYELWRIPYVIPESDHLYT
PDFLLPNGIFIETKGLWDSDDRKKHLLIREQHPELDIRLVFSSSRSKLYKGSPTS
YGEWCEKHGILFADKLIPVAGVKEPKKEVPFDKFKTKKGVKKNG
(SEQ ID NO:15)

>gi|76916|pir||S07505 endodeoxyribonuclease I (EC 3.1.21.-) - phage T3
MAGAYAARCTQGRAFRSGLEDKVSKQLESKGIKFDYELWRIPYVIPESDHLYT
PDFLLPNGIFIETKGLWDSDDRKKHLLIREQHPELDIRLVFSSSRSKLYKGSPTS
YGEWCEKHGILFADKLIPVAGVKEPKKEVPFDKFKTKKGVKKNG
(SEQ ID NO:15)

>gi|15694|emb|CAA35132.1| 3 [Bacteriophage T3]
MAGAYAARCTQGRAFRSGLEDKVSKQLESKGIKFDYELWRIPYVIPESDHLYT
PDFLLPNGIFIETKGLWDSDDRKKHLLIREQHPELDIRLVFSSSRSKLYKGSPTS
YGEWCEKHGILFADKLIPVAGVKEPKKEVPFDKFKTKKGVKKNG
(SEQ ID NO:15)

>gi|29366712|ref|NP_813757.1| putative endonuclease [Pseudomonas phage gh-1]
MAYAGPKGARTGAFRSGLEDRNAKHMDKLGVKYDFERFHINYVVPARDAKYT
PDFVLANGIIIETKGIWEVDDRKKHLLIREQYPDLDIRLVFSNSNSKIYKGSPTS
YADFCTKHGIQFADKLVPRDWLKEARKEIPQGVLVPKKGG (SEQ ID NO:16)

>gi|29243571|gb|AAO73150.1|AF493143_11 putative endonuclease [Pseudomonas phage gh-1]
MAYAGPKGARTGAFRSGLEDRNAKHMDKLGVKYDFERFHINYVVPARDAKYT
PDFVLANGIIIETKGIWEVDDRKKHLLIREQYPDLDIRLVFSNSNSKIYKGSPTS
YADFCTKHGIQFADKLVPRDWLKEARKEIPQGVLVPKKGG (SEQ ID NO:16)

===========

>gi|26988992|ref|NP_744417.1| phage endodeoxyribonuclease I [Pseudomonas putida KT2440]
MGLKYGFRSGLEERAADQLTAVGMGFTFESLVVPYTRPAKVHKYTPDFALANG
IIVETKGRFLTEDRQKQLLVKAQHPELDVRFVFSNSKTKINKRSTTTYADWCSK
NGFQYADKLVPHAWLNEPVNEASLSIIKGLSKEK (SEQ ID NO:17)

>gi|24983812|gb|AAN67881.1|AE016420_3 phage endodeoxyribonuclease I [Pseudomonas putida KT2440]
MGLKYGFRSGLEERAADQLTAVGMGFTFESLVVPYTRPAKVHKYTPDFALANG
IIVETKGRFLTEDRQKQLLVKAQHPELDVRFVFSNSKTKINKRSTTTYADWCSK
NGFQYADKLVPHAWLNEPVNEASLSIIKGLSKEK (SEQ ID NO:17)

>gi|9964626|ref|NP_064756.1| RP Endonuclease I [Roseophage SIO1]
MLNSKSSTRKRALKAGYRSGLEEQTAKDLKKRKVLFTYEETKIKWLDSKVRTY
TPDFVLPNGVIIETKGRFVAADRRKHLEIQKQFGTLYDIRFVFTNSKAKLYKGAK
SSYADWCNKHGFLYADKTIPEDWLNE (SEQ ID NO:18)

>gi|9944317|gb|AAG02601.1|AF189021_20 Roseophage SIO1 complete genome
MLNSKSSTRKRALKAGYRSGLEEQTAKDLKKRKVLFTYEETKIKWLDSKVRTY
TPDFVLPNGVIIETKGRFVAADRRKHLEIQKQFGTLYDIRFVFTNSKAKLYKGAK
SSYADWCNKHGFLYADKTIPEDWLNE (SEQ ID NO:18)

MODIFIED DNA CLEAVAGE ENZYMES AND METHODS FOR USE

CROSS REFERENCE

This application is a §371 application of international application number PCT/US2004/039288 filed on 22 Nov. 2004, which claims priority from U.S. provisional application No. 60/524,123 filed on 21 Nov. 2003, herein incorporated by reference.

BACKGROUND

Recombination between sequences on two distinct duplex DNAs, or between sequences, which are separated by an intervening sequence on the same DNA duplex, occurs in all cells capable of self-replication. Four-way Holliday junctions in DNA are a feature of recombination reactions and are generated in both homologous and site-specific recombination reactions (Lilley, D. M. J. *PNAS* 94, 9513-9515 (1997)). The penultimate stage of recombination involves resolution of the four-way junction by catalysis. The catalysis is achieved by structure-specific nucleases identified as resolvases (Aravind, L., et al. *Nuc. Acid Res.* 28:3417-3432 (2000)). Resolvases are widespread in cells and additionally are expressed by viruses. Resolvases have diverse properties. The crystal structures of a number of resolvases have been reported, including that of T7 Endonuclease I (T7 Endo I) (Hadden, J. M., et al. *Nat. Struct. Biol.* 8:62-67 (2001)).

T7 Endo I has two catalytic centers that are juxtaposed in a way that prevents the enzyme from forming a productive complex with regular linear DNA but enables it to specifically bind and cleave branched, perturbed or flexible DNA. The three-dimensional structure of T7 Endo I shows that the two catalytic domains are well separated and connected only by the β-sheet bridge (Hadden, J. M., et al. *Nat. Struct. Biol.* 8:62-67 (2001)). The bridge forms part of an extended and tightly associated anti-parallel β-sheet (β2).

T7 Endo I is a stable homodimer of 149 amino acid subunits (Parkinson, M. J. and Lilley, D. M. J. *J. Mol. Boil.* 270:169-178 (1997)). It is very basic (pI calc 9.5) and binds tightly (Kd 2 nM) to four-way junctions in dimeric form. T7 Endo I resolves four-way junctions by simultaneously introducing two nicks on the two continuous strands, at sites 5' to the junction (Déclais, A., et al. *EMBO J.* 22:1398-1409 (2003)). This structural analysis shows that T7 Endo I forms an intimately associated symmetrical homodimer comprising two catalytic domains connected by a bridge. Each catalytic domain is composed of residues 17-44 from one subunit and residues 50-145 from the other.

Resolvases including T7 Endo I are structure-specific endonucleases capable of cleaving a broad range of DNA molecules with a variety of structures such as branched structures and single-base mismatched heteroduplexes (Mashal, R. D., et al. *Nat. Genet.* 9:177-183 (1995)). This broad substrate specificity makes it difficult to identify the common structural features of the substrate that the enzyme selectively recognizes and cleaves (White, M. F., et al. *J. Mol. Biol.* 269:647-664 (1997)). The broad substrate specificity may also contribute to the toxicity of the resolvase in host cells.

It would be desirable to reduce the toxicity of the enzymes having a similar structure to T7 Endo I to facilitate their overproduction for use as reagents in molecular biology. It would also be desirable to selectively favor specific enzyme activities.

SUMMARY

An embodiment of the invention provides a modified DNA cleaving enzyme having at least 35% amino acid sequence identity with T7 Endo I, two catalytic centers separated by a β-bridge, and a mutation of at least one amino acid in the β-bridge that has an effect of altering cleavage activity.

In an embodiment of the invention, a feature of the modified DNA cleaving enzyme is reduced toxicity in a host cell permitting over-expression of the DNA cleaving enzyme.

In other embodiments of the invention, the modified DNA cleaving enzyme is capable of at least one of: cleaving cruciform structures in DNA; cleaving DNA at a site flanking a mismatch base pair; cleaving DNA in a non-sequence specific manner; nicking in a non-sequence dependent manner; and nicking opposite a pre-existing nick site. Cleavage on both strands of a DNA duplex results in a single stranded overhang of less than 11 nucleotides.

In comparison with the unmodified enzyme, the altered enzyme cleavage activity of the modified enzyme may, in certain embodiments, include a broadened enzyme specificity. For example, for the enzyme having a mutation in the β-bridge, DNA cleaving activity can occur at a site flanking a mismatch in a duplex after recognition of a mismatch containing any of A, T, G or C bases.

In another embodiment of the invention, an alteration in the enzyme cleavage activity of the modified enzyme compared to the unmodified enzyme occurs in a manganese-containing buffer. For example, the alteration in cleavage activity may be one of: maintenance of cleavage activity; reduction of non-specific nuclease activity; enhanced nicking activity opposite a pre-existing nick site; and a decreased ratio of nicking to double strand cleavage.

In another embodiment of the invention, an alteration in the enzyme cleavage activity of the modified enzyme compared to the unmodified enzyme occurs in a magnesium-containing buffer. Accordingly, the observed altered enzyme activity is selected from: an increased ratio of nicking of a cruciform structure in the DNA relative to double strand cleavage; an increased ratio of cleaved DNA of a cruciform to non-cleaved DNA; a reduced ratio of non-specific nuclease activity; and a reduction in nicking opposite a pre-existing nick site.

The altered enzyme activity of the modified enzyme can be enhanced or reduced activity by modifying reaction conditions. For example, modified reaction conditions may result from changing at least one of: pH, temperature, addition of manganese ions to a magnesium containing buffer or vice versa or changing the concentration of magnesium or manganese ions in the reaction mixture; and time of incubation of reactants.

In an embodiment of invention, the DNA cleaving enzyme is selected from gene 3 (enterobacteriophage T7), T7 endodeoxyribonuclease I, *Yersinia pestis* phage phiA1122 endonuclease, Phage Phi Ye03-12 endonuclease, Phage T3 endonuclease, phage T3 endodeoxyribonuclease, *Pseudomonas* phage gh-1 endonuclease, *psuedomonas putida* KT2440 endodeoxyribonuclease I; and Roseophage S101 RP endonuclease I.

In an embodiment of the invention, the modified enzyme has a mutation at a PA site in the β-bridge. For example, this mutation may be a deletion (ΔPA (where (Δ) corresponds to "deletion"), or a substitution of PA such as a single amino acid, a dipeptide, a tripeptide or a tetrapeptide substitution.

Examples of substitutions include: PA/A, PA/AA, PA/PGA, PA/PAPA, PA/K, PA/G, PA/D and PA/P (where PA/A corresponds to a substitution (/) of PA dipeptide with A amino acid).

In an embodiment of the invention, the PA dipeptide is located at position 46 and 47 in SEQ ID. No. 12.

In an embodiment of the invention, a nucleic acid is provided that includes a DNA sequence that substantially corresponds to SEQ ID NO:1 wherein at least one mutation has been introduced into the nucleotide sequence corresponding to the β-bridge. For example, the mutation may be included at a site, which encodes the PA in the β-bridge. In this example, the mutation at the site that encodes PA may be any of a substitution or deletion such that the substituted nucleic acid encodes a single amino acid, a dipeptide, a tripeptide and a tetrapeptide. In a further example, the at least one mutation results in an amino acid change selected from PA/A, PA/AA, PA/PGA, PA/PAPA, ΔPA, PA/K, PA/G, PA/D and PA/P.

In embodiments of the invention, a vector is provided that includes any of the above examples of nucleic acids. In addition, a host cell is provided that includes any vector that includes a nucleic acid as described above.

In a further embodiment of the invention, a kit is provided that contains at least one of: a DNA cleaving enzymes in which a mutation has been introduced into the β-bridge as described above, a nucleic acid encoding the enzyme, a vector containing the nucleic acid, or a host cell containing the vector described above.

In a further embodiment of the invention, a method is provided for modifying enzyme catalytic activity that includes: selecting an enzyme having two catalytic centers connected by a β-bridge, the catalytic centers being located at reciprocal stereo-geometric positions in the enzyme; and changing the reciprocal stereo-geometric position of the two catalytic centers by introducing a mutation into the β-bridge.

In a further embodiment of the invention, a method is provided for determining whether a DNA substrate has a single nucleotide polymorphism (SNP). The method includes the steps of: contacting the DNA substrate with a modified DNA cleaving enzyme as described above; and determining from the cleavage product whether the DNA substrate has the SNP. It can further be determined which nucleotide forms a SNP and the location of the SNP (see for example FIG. 11)

In a further embodiment of the invention, a method is provided of forming a shotgun cloning library, that includes the steps of (a) incubating a modified DNA cleaving enzyme as described above with a DNA to form non-sequence specific cleavage fragments of the DNA that are ligatable; the ligatable DNA being capable of insertion into a vector for cloning in a host cell; and forming the shotgun cloning library.

In a further embodiment of the invention, a method for mapping nicks in a DNA is provided having the following steps: (a) incubating an enzyme according to the above with the DNA in a manganese-containing buffer; (b) permitting nicking to occur across from a pre-existing nick site to form double-stranded DNA with single strand overhangs; and (c) mapping the nicks in the DNA.

In a further embodiment of the invention, a method is provided for over-expressing T7 endonuclease 1, that includes selecting a host cell as above and over-expressing the T7 endonuclease 1.

BRIEF DESCRIPTION OF THE FIGURES

In the figure descriptions below, unless otherwise stated, "buffer" refers to standard buffer and $Mn^{2+}$ or $Mg^{2+}$ buffer refers to the standard buffer plus 2 mM of the metal salt.

Cultures of ER2566 containing pME, pME(PA/A) and pME(ΔPA) were grown at 37° C. to mid-log phase, then at 30° C. with 0.5 mM IPTG for 5 hours. The induced cells were harvested by centrifugation, suspended in standard buffer (20 mM Tris pH 7.6, 50 mM NaCl and 1 mM EDTA) and opened by sonication. After cell debris was removed by centrifugation, the crude cellular extracts were applied onto an amylose column. After the crude extracts flowed through, the column was washed with the buffer extensively. The fusion protein was eluted with the buffer containing 10 mM maltose. SDS-PAGE was carried out on a 10-20% gradient gel. 30 μl samples of the induced culture were used for each lane.

Lanes are labeled as follows: C, crude cellular extracts, F, the flow through fraction and E, maltose elution fraction.

Figure 2:
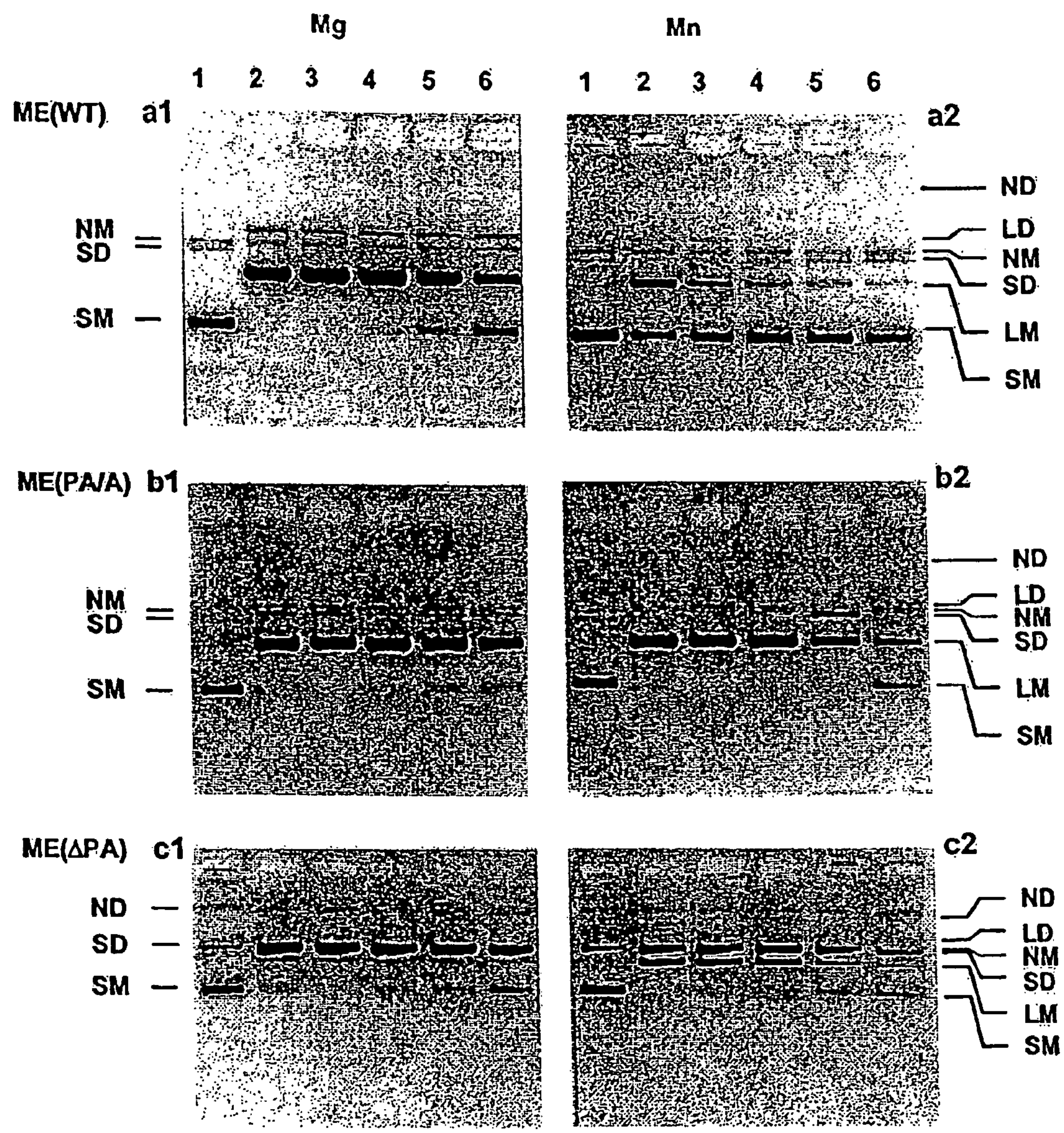

FIG. 2 shows determination of enzyme activity by titration assay. 1 μg of pUC(AT) in 20 μl of either 2 mM $MgCl_2$ or 2 mM $MnCl_2$ in standard buffer was incubated with variable amounts of enzyme at 37° C. for 30 minutes. Adding DNA sample buffer on ice stopped the reactions. The samples were resolved on a 1.2% agarose gel with ethidium bromide.

Lane assignments in all panels are:

lane 1, no enzyme; lane 2, 5 ng enzyme; lane 3, 2.5 ng enzyme; lane 4, 1.25 ng enzyme; lane 5, 0.63 ng enzyme; lane 6, 0.32 ng enzyme Panels are:

Panel a1 shows ME(WT) in $Mg^{2+}$ buffer

Panel a2 shows ME(WT) in $Mn^{2+}$ buffer

Panel b1 shows ME(PA/A) in $Mg^{2+}$ buffer

Panel b2 shows ME(PA/A) in $Mn^{2+}$ buffer

Panel c1 shows ME(ΔPA) in $Mg^{2+}$ buffer

Panel c2 shows ME(ΔPA) in $Mn^{2+}$ buffer

Figure 3:
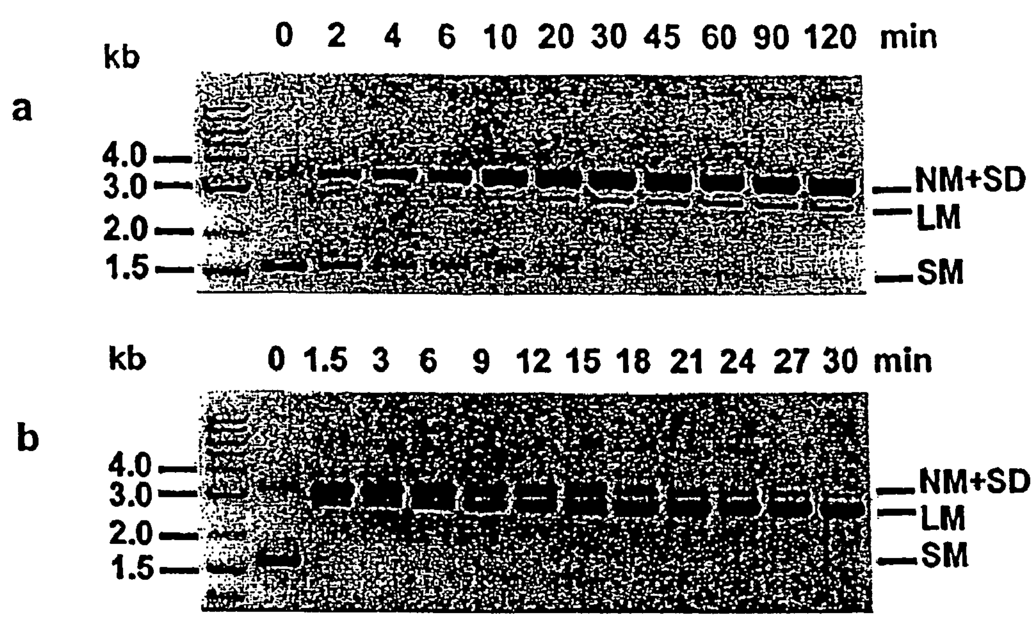

FIG. 3 shows cleavage of pUC(AT) by ME(ΔPA) in two step reactions.

In Panel a, pUC(AT) was incubated with the enzyme (DNA/enzyme: 1 μg/1.5 ng) at 37° C. in $Mg^{2+}$ standard buffer. At variable time points, an aliquot of sample was withdrawn and mixed with DNA sample buffer on ice. The collected samples were resolved on a 1.2% agarose gel with ethidium bromide.

In Panel b, the experiment was performed as in Panel A, except the DNA/enzyme was 1 μg/0.5 μg.

Figure 4:
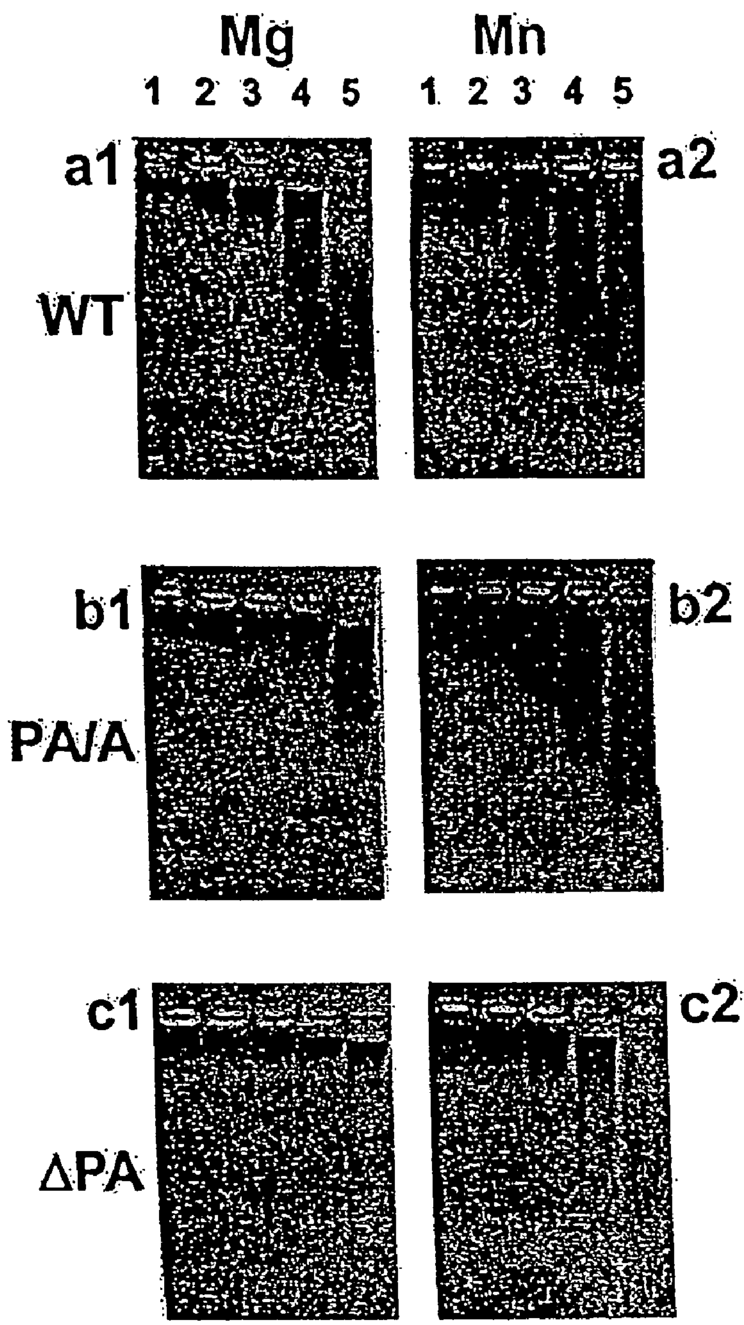

FIG. 4 shows the determination of non-specific nuclease activity by gel electrophoresis. 1 μg of lambda DNA was incubated with variable amounts of enzyme in 20 μl of either $Mg^{2+}$ or $Mn^{2+}$ buffer at 37° C. for 30 minutes. The reaction was stopped by adding DNA sample buffer, then analyzed by agarose gel electrophoresis.

Lanes: lane 1, no enzyme added; lane 2, with 3 ng of enzyme; lane 3, 16 ng; 4, 80 ng; 5, 400 ng In Panel a1, ME in $Mg^{2+}$ buffer.

In Panel a2, ME in $Mn^{2+}$ buffer.

In Panel by, ME(PA/A) in $Mg^{2+}$ buffer.

In Panel b2, ME (PA/A) in $Mn^{2+}$ buffer.

In Panel c1, ME(ΔPA) in $Mg^{2+}$ buffer.

In Panel c2, ME(ΔPA) in $Mn^{2+}$ buffer.

FIG. 5 shows the determination of nick site cleavage activity of the DNA cleaving enzyme.

Figure 5A:
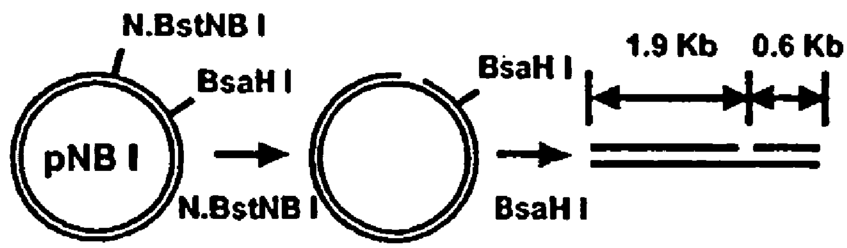

FIG. 5A shows pNBI plasmid having a nick site and a restriction site. The plasmid was nicked by N.BstNB1 and then digested with BsaHI to yield a linearized double-stranded molecule containing a nick.

Figure 5B:
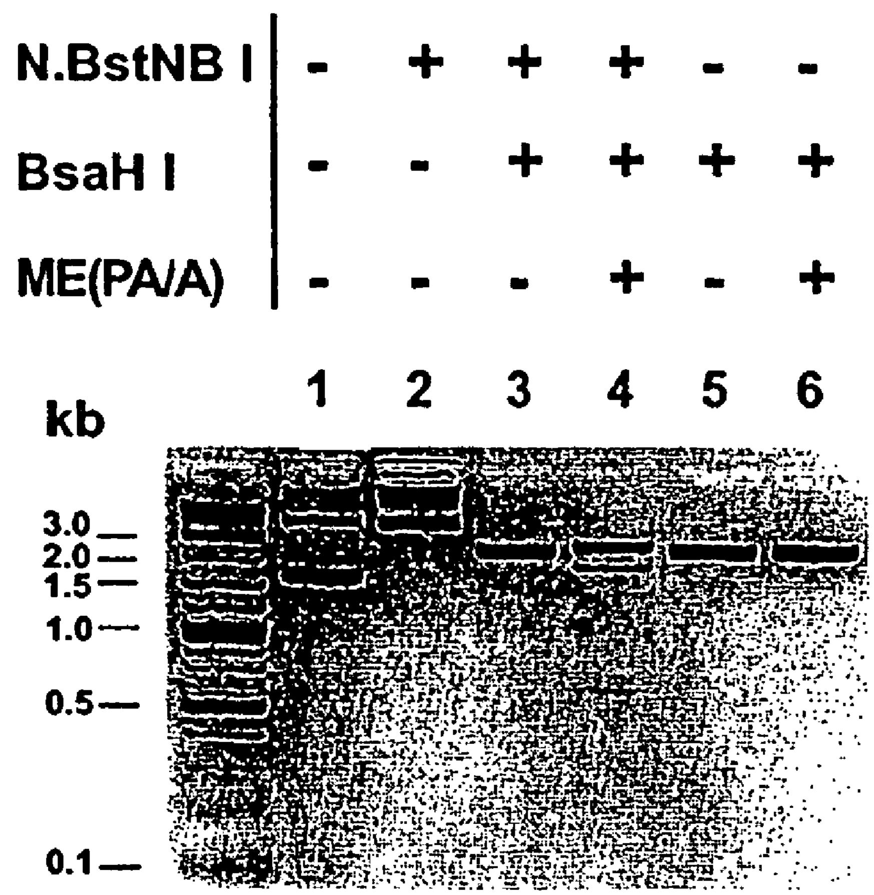

FIG. 5B shows the results of different enzyme mixtures by gel electrophoresis.

Lane 1, pNB I DNA;

Lane 2, pNB I digested with N.BstNB I;

Lane 3, with N.BstNB I, then with BsaH I;

Lane 4, with N.BstNB I and BsaH I, then with long of ME in $Mg^{2+}$ buffer at 37° C. for 30 minutes;

Lane 5, with BsaH I;

Lane 6, with BsaH I, then with ME.

Figure 6:
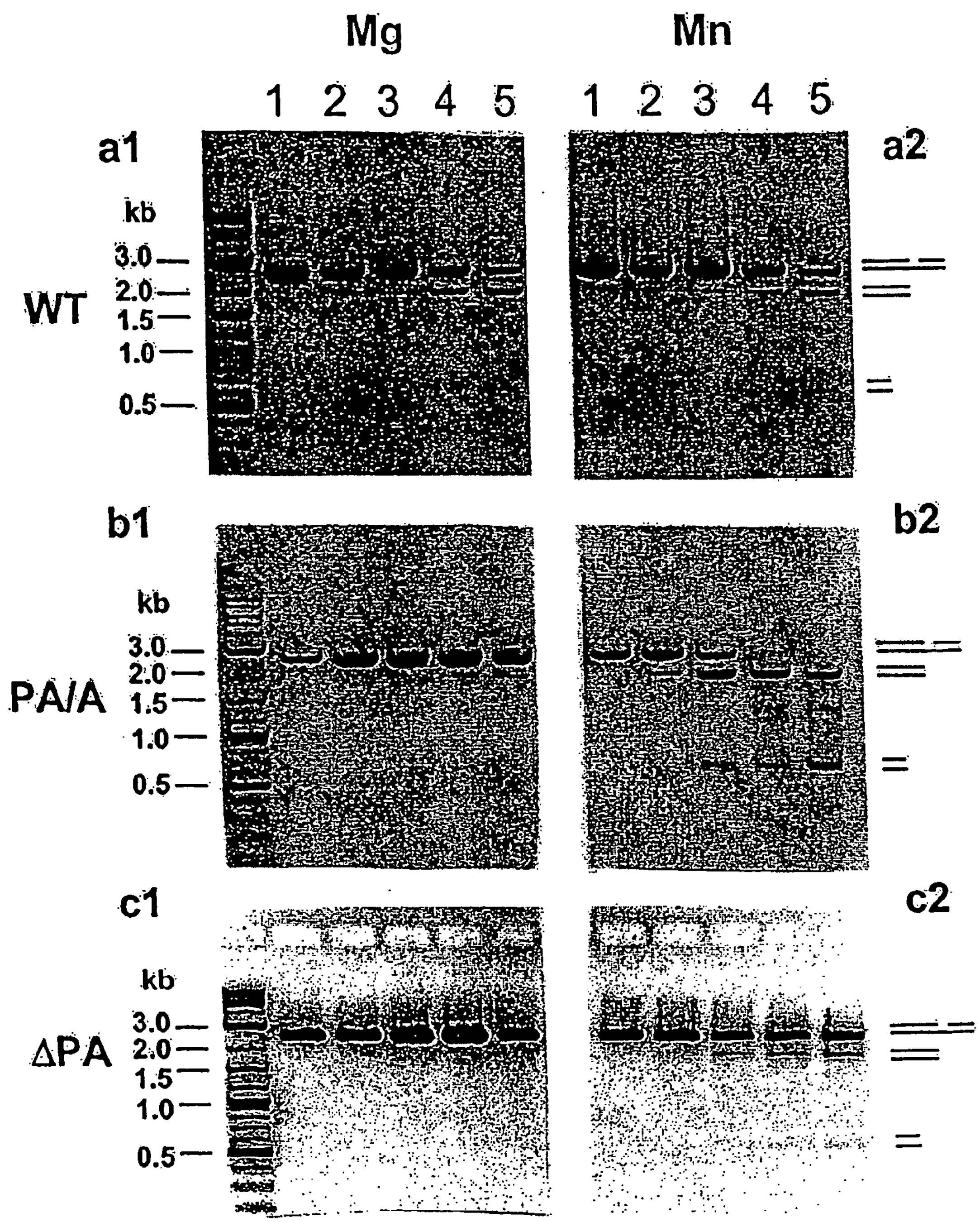

FIG. 6 shows the determination of nick site cleavage in the presence of different metal ions. 1 μg of the prepared substrate incubated with variable amounts of modified or unmodified enzyme at 37° C. for 30 minutes in either $Mg^{2+}$ or $Mn^{2+}$ buffer. The digests were resolved on agarose gel.

Lanes for all panels: Lane 1, no enzyme; Lane 2, with 2.5 ng of enzyme; Lane 3, 5 ng; Lane 4, long; Lane 5, 20 ng.

In panel a1, the unmodified enzyme ME (WT) was used in $Mg^{2+}$ buffer.

In panel a2, ME (WT) in $Mn^{2+}$ buffer.

In panel b1, ME(PA/A) in $Mg^{2+}$ buffer.

In panel b2, ME(PA/A) in $Mn^{2+}$ buffer.

In panel c1, ME(ΔPA) in $Mg^{2+}$ buffer.

In panel c2, ME(ΔPA) in $Mn^{2+}$ buffer.

Figure 7:
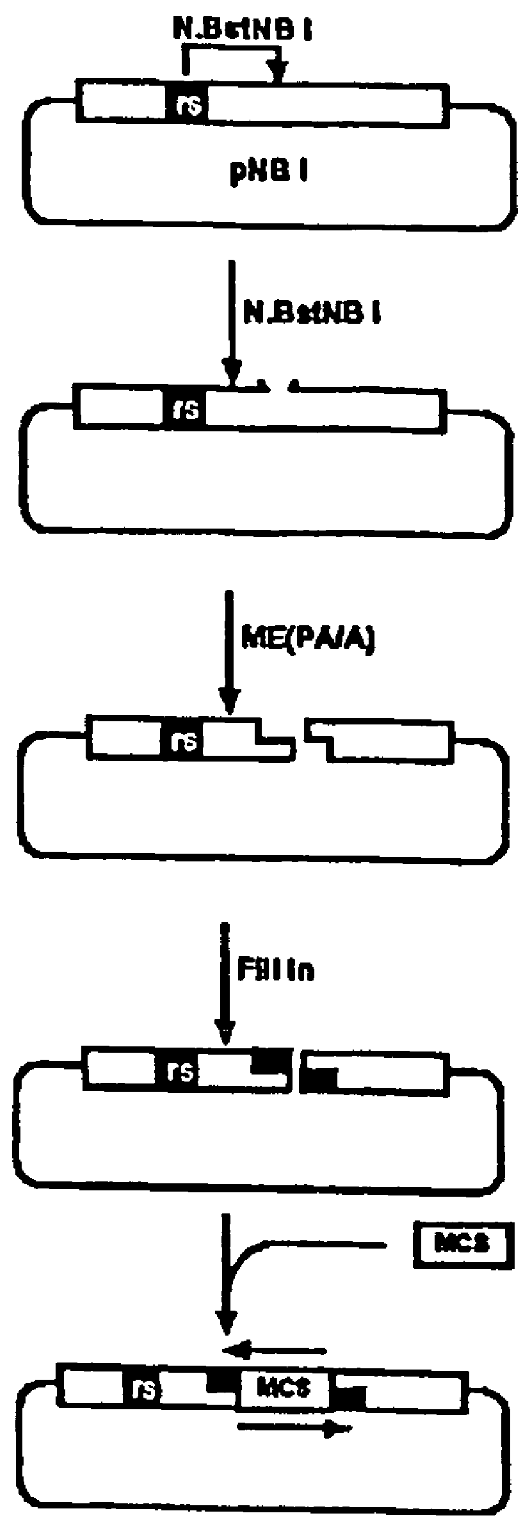

FIG. 7 shows the determination of the cleavage pattern at a DNA nick site by a modified DNA cleaving enzyme. Schematic representation of the method for analyzing the cleavage pattern at a nick site is provided.

Figure 8:
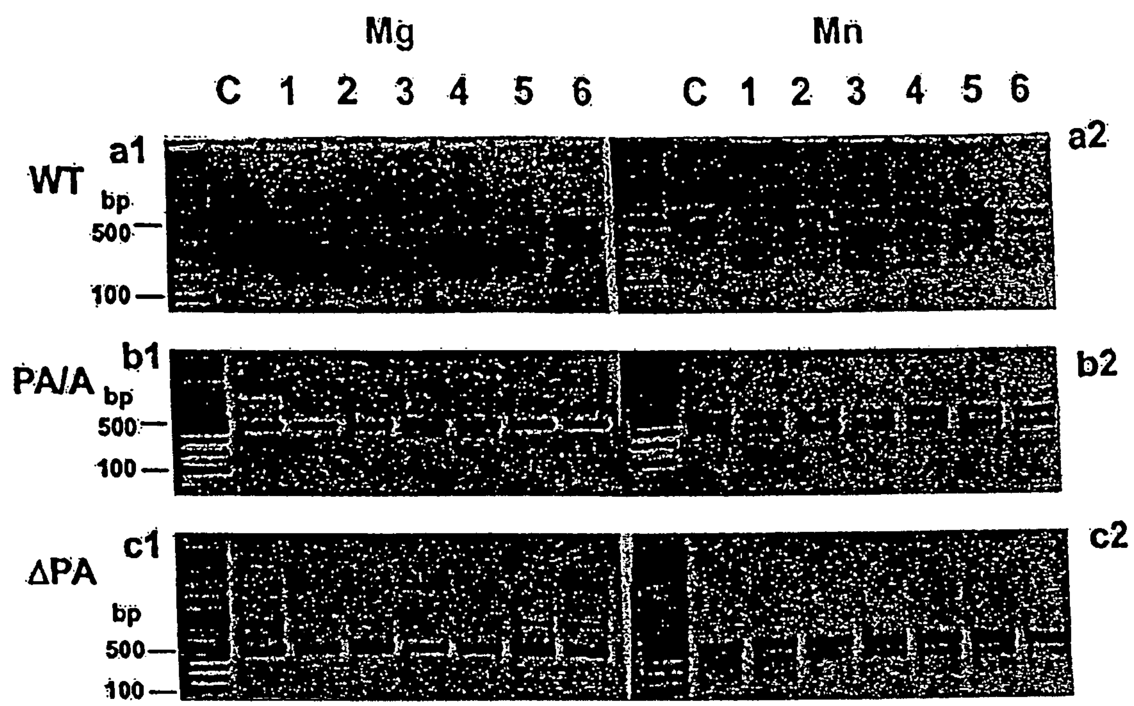

FIG. 8 shows the determination of DNA cleavage at single base mismatches by modified and unmodified DNA cleaving enzyme using hybrid mixtures as substrates. 0.5 μg of each of hybrid mixture substrates was incubated with 20-30 ng of enzyme in a 20 μl reaction at 37° C. for 30 minutes. The digests were resolved on an agarose gel.

Lanes for each panel: lane C, PCR product pcrAAT DNA or pcrACT as control; lane 1, hmAAT×ACT; lane 2, hmAAT×AGT; lane 3, hmAAT×ATT; lane 4, hmACT×AGT; lane 5 hmACT×ATT; and lane 6, hmAGT×ATT.

In panel a1, ME in $Mg^{2+}$ buffer

In panel a2, ME in $Mn^{2+}$ buffer.

In panel b1, ME(PA/A) in $Mg^{2+}$ buffer.

In panel b2, ME(PA/A) in $Mn^{2+}$ buffer.

In panel c1, ME(ΔPA) in $Mg^{2+}$ buffer.

In panel c2, ME(ΔPA) in $Mn^{2+}$ buffer.

FIG. 9 shows how DNA substrates are generated for determination of enzyme activity on each individual single base mismatched DNA.

Panel A shows a schematic representation of preparation of an individual DNA heteroduplex with a definitive single-base mismatch. For making positive strand DNA, non-phosphorylated forward primer, pr-1 and phosphorylated reverse primer, P-pr-2 were used for PCR. The bottom strand, or the negative strand of the PCR product was removed by lambda exonuclease. The negative strand DNA was prepared by the same method as the positive one except that phosphorylated forward primer P-pr-1 and non-phosphorylated reverse primer pr-2 were used.

Panel B is an example for generating a single-base mismatched heteroduplex by annealing two purified single stranded DNAs Lane 1, double stranded DNA produced by PCR, pcrAAT or pcrACT;

Lane 2, the positive (top) strand ssACT(+) isolated from pcrACT;

Lane 3, the negative (bottom) strand ssAAT(−) isolated from pcrAAT;

Lane 4, single-base mismatch (C/T) heteroduplex produced by annealing the purified positive strand with the negative one.

FIG. 10 shows the determination of DNA cleavage by modified or unmodified DNA cleaving enzymes at individual single-base mismatches. 16 DNA duplexes were generated by annealing each one of the 4 isolated positive strands with each one of the 4 negative strands. Among them 4 were regular (perfect match) duplexes; 12 were heteroduplexes with single-base mismatches. 0.2-0.3 μg of the prepared duplex DNA were incubated with 10-15 ng of enzyme in 10 μl of either $Mg^{2+}$ or $Mn^{2+}$ buffer at 37° C. for 20-30 minutes. The digests were resolved on agarose gels.

In panel a1 and a2, different duplexes were incubated with ME in $Mn^{2+}$ buffer.

In panel b1 and b2, they were incubated with PA(PA/A) in $Mn^{2+}$ buffer.

Figure 11:
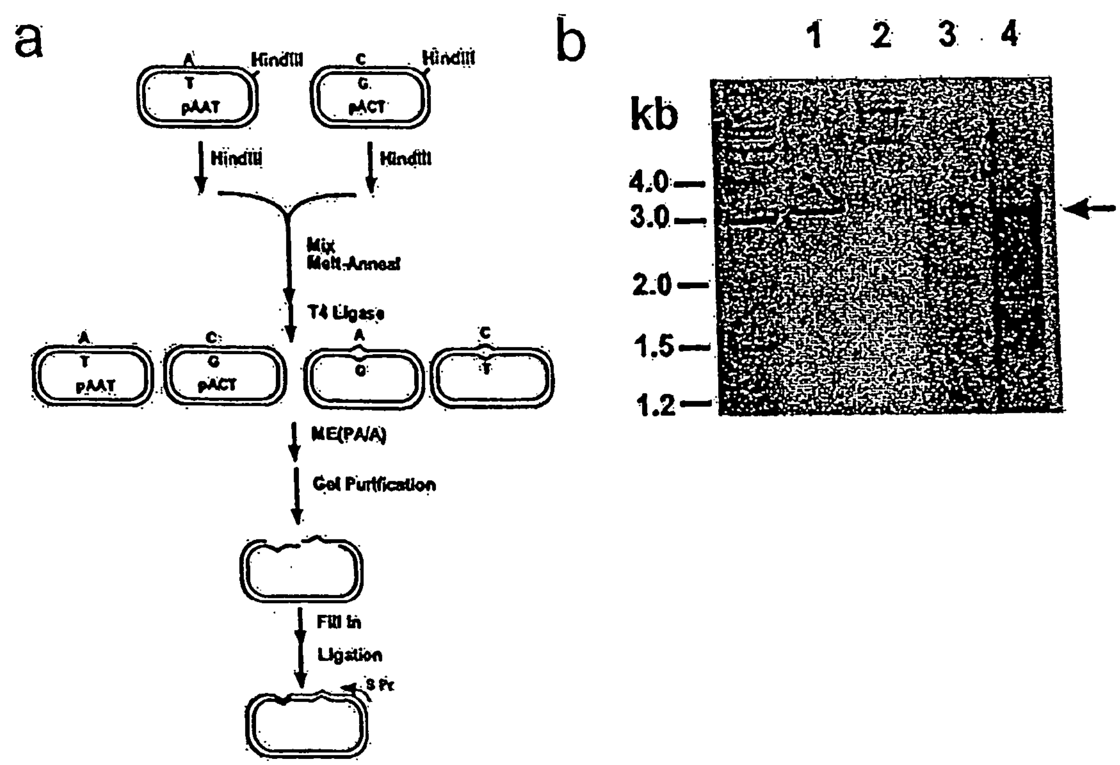
Figure 11:
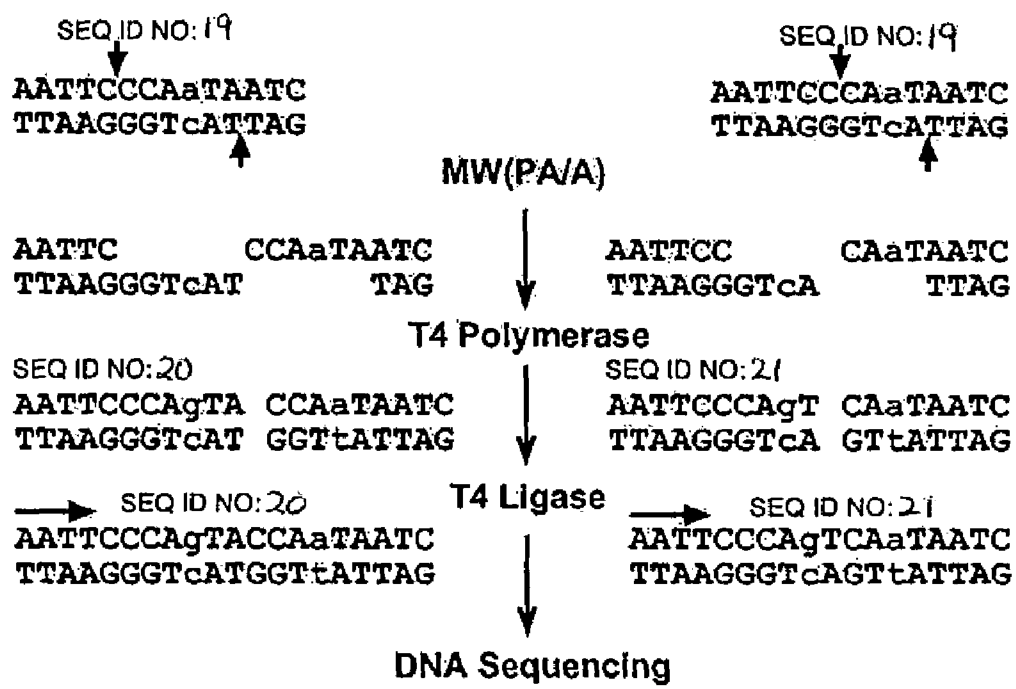

FIG. 11 shows the determination of the cleavage pattern by a modified DNA cleaving enzyme at base mismatch sites.

Panel a is a schematic representation of the experiment.

Panel b shows the experimental intermediate products resolved on a 1.2% low-melting agarose gel.

Lane 1, the mixed open plasmids after melt-anneal treatment;

Lane 2, after treatment with T4 ligase;

Lanes 3 and 4, after cleavage with ME(PA/A) in $Mn^{2+}$ buffer followed by blunting the ends with T4 DNA polymerase. The arrow symbol indicates the linear plasmid band that was excised and used for transformation after ligation.

Panel c shows a DNA sequences (SEQ ID NOS:19, 20 and 21) correlating to (a) and (b).

Figure 12:
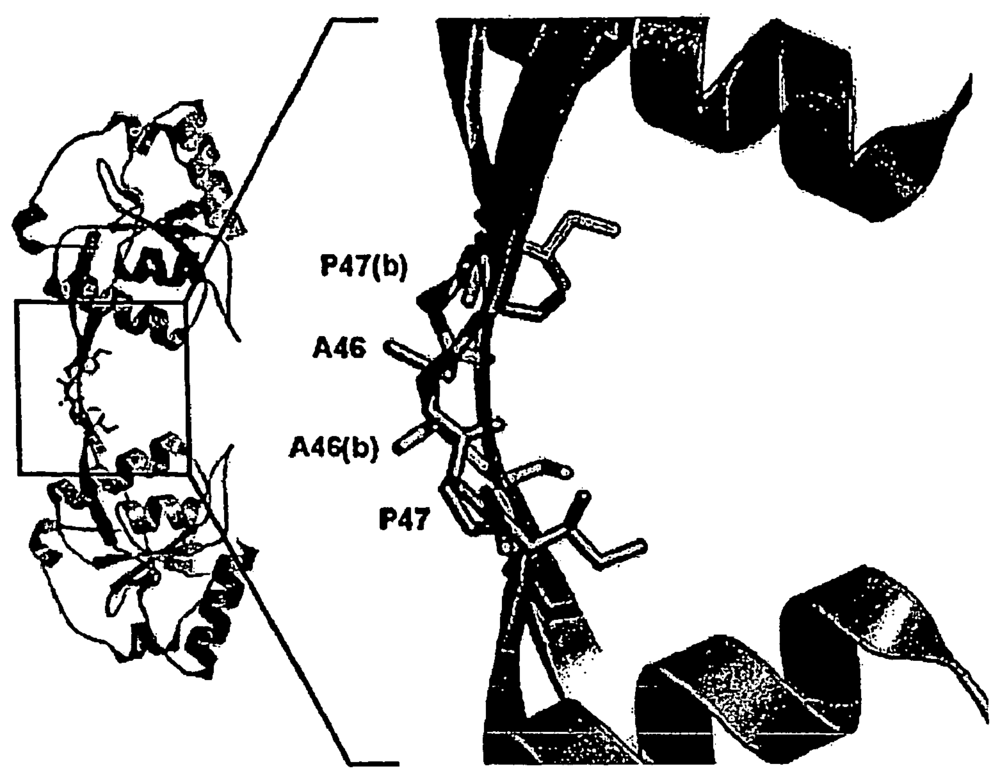

FIG. 12 shows the three-dimensional structure of T7 Endo I and the β-bridge. The homodimer is shown at left with one monomer displayed in light gray and the other in dark gray. At the right is a detail of the β-bridge showing the positions of the proline and alanine residues mutated in this study. Residues marked with (b) refer to the second monomer (light gray).

FIG. 13 shows the DNA and amino acid sequences for unmodified T7 Endo I (SEQ ID NOS:1 and 12).

FIG. 14 shows protein sequences (SEQ ID NOS:12, 13, 14, 15, 16, 17, 18, 22 and 23) from phage that have at least 35% amino acid identity with the T7 Endo I sequence (SEQ ID NO:12) in FIG. 13.

Figure 15:
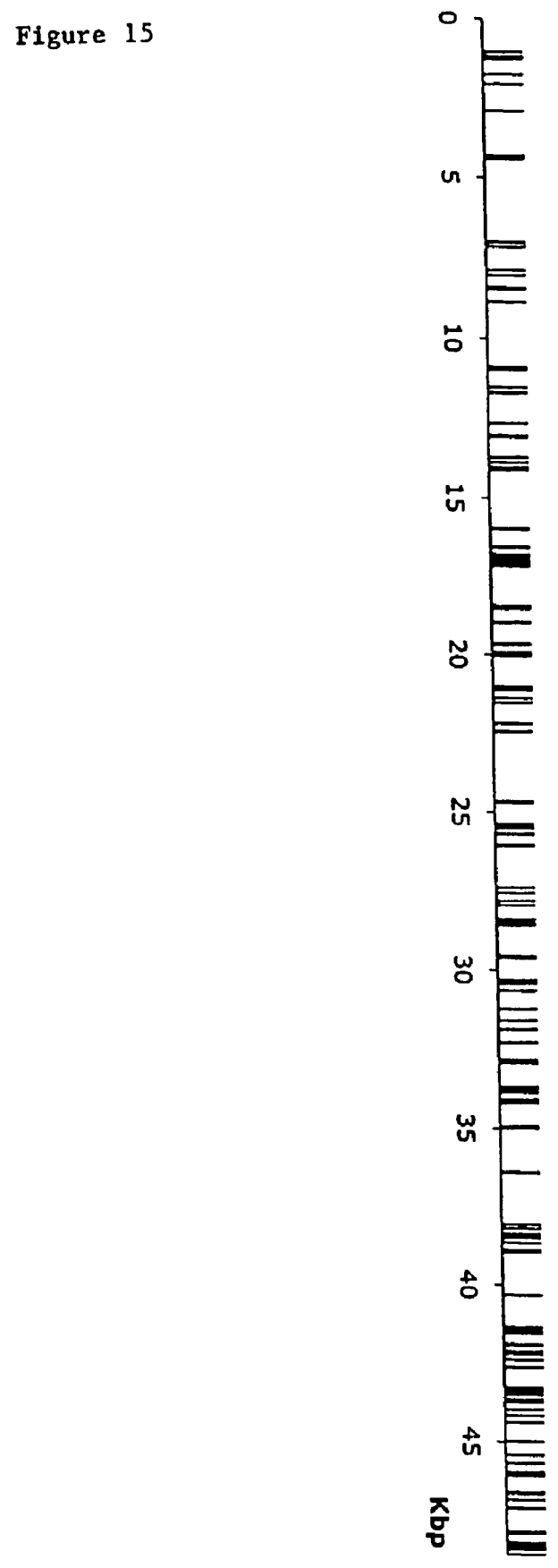

FIG. 15 is a map of cleavage sites in lambda showing that nicking with modified T7 Endo I is random. Full length linear lambda phage DNA was digested with the ME fusion enzyme containing the PA to A sequence modification (ME[PA/A]) in the presence of 2 mM $MnCl_2$. DNA fragments from the reaction were purified by phenol extraction and EtOH precipitation. After resuspension, the ends of the DNA fragments were filled in using T4 DNA polymerase and dNTPs (12° C. or room temperature, 30 min). The blunt-ended fragments were inserted into the EcoRV site of cloning vector Litmus28 by adding aliquots of the ligation reaction to gel-purified Litmus28 that was previously digested with EcoRV and dephosphorylated with Calf Intestinal Phosphatase (CIP). The ligation mixture was used to transform competent *E. coli* TB1 cells. DNA was purified from ampicillin resistant transformants and the inserts sequenced. Recovered sequence was examined to locate vector-insert junctions and junctions between normally non-contiguous fragments of lambda DNA. The endpoints of the junctions were mapped to the complete lambda DNA sequence. The distribution of cleavage sites on the lambda genome are shown here using ME[PA/A] where this distribution is random.

DETAILED DESCRIPTION

Abbreviations: MBP, maltose binding protein, ME, maltose binding protein—T7 endonuclease 1 conjugate, PCR, polymerase chain reaction, PAGE, polyacrylamide gel electrophoresis, MCS, multiple cloning site, dNTP, deoxyribonucleotide triphosphate, ATP, adenosine triphosphate, SNP, single nucleotide polymorphism. The term nuclease is used interchangeably with endonuclease.

"Cleavage" refers to a break in one or both of the strands of a duplex at opposite positions.

"Opposite positions" refers to sites on the top and bottom strands of the duplex DNA, where the sites are separated by less than 11 bases from each other.

The present embodiments apply to a class of enzymes characterized by a similar architecture to T7 Endo I and including T7 Endo 1 namely having two catalytic domains and a 5-bridge (see for example, FIG. 12). Enzymes in this class can be identified using the Conserved Domain Architecture Retrieval Tool (CDART) program of the National Center for Biotechnology Information (Geer, Lewis Y., et al. *Genome Research* 12:1619-1623 (2002)) or by other predictive programs, based on searches employing the sequence of T7 Endo I (FIG. 13).

Examples of enzymes identified in this manner include: T odd phages or related viruses including Enterobacteria phage T7, NP_848275, endonuclease of *Yersinia pestis* phage phiA1122; NP_813757 putative endonuclease of *Pseudomonas* phage gh-1; NP_744417, phage endodeoxyribonuclease I of *Pseudomonas putida* KT2440; NP-523312, endonuclease of Bacteriophage T3; NP_064756, RP Endonuclease I of Roseophage SIO1; and NP_052083, endonuclease of Bacteriophage phiYeO3-12. In addition other related phages such as SP6, bacteriophage phiKMV, Enterobacteria phage K1-5, Vibriophage VpV262, BA14, BA127 and BA156 may encode similar enzymes.

Examples of enzymes having at least 35% amino acid identity with T7 Endo I are listed in FIG. 14.

The reciprocal stereo-geometric positions of the two catalytic centers in an enzyme of the above class can be changed by introducing mutations into the bridge without changing the catalytic centers per se, using genetic or biochemical means. Consequently, as exemplified herein, mutations were introduced into the β-bridge site without interfering with the folding and function of the catalytic domain (Example 1). Embodiments of the invention are not intended to be limited by (a) the exemplified methods for introducing mutations into sites in the β-bridge or (b) any particular location of the mutation within the bridge. The term "mutation" is intended to mean deletion, substitution or addition of one or more amino acids in the enzyme.

Mutations in the bridge portion of the enzyme resulted in shifting the enzyme activity profile to different substrates and in alteration of the reaction kinetics and distribution of the final products. Additionally, mutations in the bridge portion result in altered enzyme activity profiles in different salt solutions. A practical consequence of the observed changes in properties of a modified enzyme compared with a unmodified enzyme is the reduced toxicity of the enzyme activity in vivo while enzyme activity is preserved or enhanced in vitro. Consequently, the modified enzyme can be cloned and overexpressed in host cells because of its reduced toxicity to the host cell. This makes it possible to produce amounts of enzyme suitable for its practical use as a reagent for molecular biology applications.

The change in the activity profile of the modified enzyme as a result of one or more mutations was achieved when (i) one or more mutations were introduced in the β-bridge segment that connects the two well-separated catalytic domains, and/or (ii) the reaction conditions were manipulated. For example, the metal ion composition of the reaction buffer was selected to provide an altered activity profile for the enzyme. In the Examples, magnesium or manganese ions were included in the reaction buffer. These buffers may also be used together to further modify the enzyme activity of the mutants. For example, if manganese ions are added to the reaction mixture containing magnesium ions, the non-sequence specific nicking can be reduced. The use of metal ions other than magnesium or manganese, either alone or together with magnesium or magnesium at various concentrations in the reaction buffer is not precluded.

In embodiments of the invention, computational analysis of the T7 Endo I structure and in particular the β-bridge revealed that the bridge constitutes part of the dimer interface, and that residues are bound to each other by hydrogen bonds except for the two residues, P46 and A47, at the bridge center (FIG. 12). The two residues are located at the geometrical center of the protein, rendering it flexible.

Genetically changing the distance between the two catalytic centers was achieved by introducing mutations into the bridge site of the protein. For example, for T7 Endo I, PA/A, PA/AA, PA/PGA, PA/PAPA, ΔPA, PA/K, PA/G, PA/D and PA/P mutants were made with altered enzyme activity which was established in reaction buffers containing magnesium or manganese ions using a variety of DNA substrates including mismatch duplex DNA, duplex DNA containing nicks, unnicked duplex DNA and DNA having cruciform structures. The conformational flexibility of a protein having a structure similar to T7 Endo I contributes to the broad substrate specificity of the enzyme. Surprisingly, nucleotide substitutions in the β-bridge that were of variable length (single amino acid, dipeptide, tripeptide or tetrapeptide), negatively charged, positively charged, or neutral in charge, flexible in structure or inflexible in structure revealed altered enzyme activities of the type described herein.

Approximately twenty-four β-bridge site mutants were generated. The proteins were purified and characterized (see for example, Example 1) All the mutations in some way altered the activity profile of the enzyme. Two active deletion mutants, ME(PA/A) and ME(ΔPA), were characterized extensively (see Example 1). As expected, the two catalytic domains in the mutants were folded correctly and were fully active, since both could resolve cruciform DNA with an efficiency similar to that of the wild type protein. For resolving cruciform structures, the wild type enzyme required $Mg^{2+}$ for its activity. The activity was reduced by 20 fold or more if $Mg^{2+}$ was replaced with $Mn^{2+}$. For the two mutants, the metal ion requirement was relaxed. The mutant proteins were almost equally active in either $Mg^{2+}$ or $Mn^{2+}$ buffer. However, the kinetics and the final products with ME(ΔPA) were changed. This mutant could no longer simultaneously cleave both strands across the cruciform structure on plasmids. Instead, it nicked one strand first at the site in a rapid reaction, resulting in relaxation of the cruciform, then cleaved the other strand at the generated nick in a separate slow reaction.

For cleavage of DNA at nicks or base mismatches and for the non-sequence specific nuclease activity, the requirements for metal ions among the enzyme and its mutants were shifted again. This time the wild type ME remained about equally active in either $Mg^{2+}$ or $Mn^{2+}$ buffer. For the mutants, however, these activities, were significantly reduced in $Mg^{2+}$ buffer. $Mn^{2+}$ became the required divalent metal ion. In $Mn^{2+}$ buffer, ME(PA/A) could recognize and cleave DNA at nick sites and at certain types of single-base mismatch sites even more efficiently than its wild type counterpart.

One of ordinary skill in the art will appreciate that a duplex DNA can be described as having a top strand and a bottom strand and that a mismatch occurs when a nucleotide at a position on the top strand is not complementary to the nucleotide at the same position on the bottom strand. Cleavage with the DNA cleaving enzyme can cause at least one of (a) a break at a 3' flanking site of the mismatched nucleotide on the top and bottom strands or (b) a break at the 5' flanking site of the mismatch on the top and bottom strands where the flanking site is preferably less than about 11 nucleotides from the mismatch.

Mutants of enzymes in which amino acids in the bridge have been altered or deleted can be significantly less toxic than the wild type enzymes in vivo. Mutants such as ME (PA/A) appear to have significantly reduced non-specific nuclease activity in the presence of $Mg^{2+}$ (present in the host cell in millimolar concentrations). This makes it possible to over-express a mutant T7 endonuclease I such as ME(PA/A). Moreover, the mutant has enhAnced resolvase activity in $Mn^{2+}$ (not present in the host cells) compared with the wild-type enzyme.

Enzymes belonging to the T7 endonuclease class (including proteins with at least 35% identity in amino acid sequence), in which one or more mutations have been introduced into the protein outside the catalytic domains and preferably within the bridge between the catalytic domains, have advantageous properties. Examples of advantageous properties as exemplified by T7 Endo I are:

1. The unmodified enzyme is toxic to cells while the modified enzyme is not thereby permitting cells to overexpress the mutant enzyme (Example 1)

2. Cleavage of cruciform structures. The unmodified enzyme ME(WT) had 20 fold reduction of activity in manganese buffer compared with its activity in magnesium buffer. In contrast, modified enzymes ME (PA/A) and ME (ΔPA) showed similar activity in the different buffers. However, ME (ΔPA) generated nicked DNA or linear DNA in equal amounts whereas ME(PA/A) produced double strand breaks (Example 2). This altered activity permits resolution of branched DNA.

3. The unmodified and the modified DNA cleaving enzymes both can find a nick in double-stranded DNA and cleave against the nick resulting in non-sequence specific cleavage of double-stranded DNA into fragments with 3 or 4 base overhangs (Example 2). However, the modified enzyme has greater cleavage activity in manganese buffer than in magnesium containing buffer. This property has utility in nick site mapping.

4. Both modified and unmodified enzymes have non-specific nuclease activity but the modified enzyme has less nuclease activity in magnesium containing buffer than the wild-type enzyme. The modified enzyme has greater nuclease activity of an amount comparable to the unmodified enzyme in manganese-containing buffers. Non-specific nuclease cleavage can provide random ligatable DNA sequences suitable for shotgun or other types of cloning. An advantage of this approach over the use of, for example, DNase I is that it is possible to control the size of the fragments and to avoid shredding the DNA of interest into tiny pieces.

5. Both modified and unmodified enzymes recognize single base mismatches. However, the modified enzyme has greater activity and recognizes a wider range of substrates than the unmodified enzyme in manganese buffer. For analysis of single nucleotide polymorphisms (SNPS), the target DNA is denatured and hybridized to related DNA, which lack the polymorphisms. This results in single base mismatches of which there are 8 possibilities: A to A, A to G, A to C, C to T, C to C, G to G, G to T and T to T. These can all be recognized by the modified enzyme (Example 2). These modified enzymes provide a useful tool for SNP detection analysis utilizing mismatch detection.

A DNA cleaving enzyme having at least 35% amino acid identity with T7EndoI and having two catalytic centers separated by a β-bridge, where the β-bridge contains a mutation that results in altered enzyme activity as described herein can be provided in a kit with a suitable buffer, for example, containing manganese ions or magnesium ions as appropriate for the desired function according to above. The kit may additionally contain a DNA size ladder. Instructions may further be included in the kit. Alternatively, the kit may include a plasmid encoding the endonuclease or indeed a transformed host cell preparation containing a recombinant vector expressing the mutated nicking endonuclease.

All references cited herein are incorporated by reference. In addition, U.S. provisional application Ser. No. 60/524,123 filed Nov. 21, 2003 and Guan et al. *Biochemistry* 43:4313-4322 (2004) are herein incorporated by reference.

EXAMPLES

Example 1

Generation of Mutations at the Bridge Site and Over-Expression of the Modified Enzymes Materials and Methods Restriction enzymes, nicking enzyme N.BstNB I, DNA polymerases, T4 ligase, T4 DNA kinase, β-agarase, λ Exonuclease, the maltose-binding protein (MBP) protein fusion expression and purification system including plasmid pMAL-c2x, the host *E. coli* strains TB1 and ER2566, Factor Xa protease, the cruciform structure-containing plasmid pUC (AT) and plasmid LITMUS28 were obtained from New England Biolabs Inc. (New England Biolabs, Inc., Beverly, Mass.). Synthetic oligonucleotides were synthesized using standard techniques. T7 phage DNA encoding T7 Endo I has a sequence corresponding to SEQ ID NO:1.

Method for Recombinant DNA and Mutagenesis

DNA manipulation and site-directed mutagenesis (Kunkel, *Proc. Natl. Acad. Sci. USA.* 82(2):488-92 (1985 January)) or by PCR were carried out as described in Molecular Cloning by Sambrook et al. (Sambrook, J. and Russell, D. W. (2001) *Molecular Cloning: a Laboratory Manual*, pub. Cold Spring Harbor Laboratory, Cold Spring Harbor, N.Y. (2001)).

Cloning T7 EndoI Mutants

For cloning T7 Endo I from phage chromosomal DNA by PCR, two primers were used:

```
oligo-1: CCCGAATTCATGGCAGGTTACGGCGCT; (SEQ ID NO: 2
and

oligo-2: CCCCCAAGCTTATTTCTTTCCTCCTTT  (SEQ ID NO: 3)
```

The PCR product was treated with restriction enzymes, and cloned into the Hind III-EcoR I site of plasmid pUC19, resulting in plasmid pEndo I. For construction of pEndo(Δβ2) (where Δβ2 is deletion of the second β sheet) and pME(Δβ2) from pEndo I, two sequential PCRs (two-step PCR) were performed. In the first step pEndo I was used as template.

Oligo-1 and oligo-4 (TGGAAGTAAGMGTCTGGCCACTCTTCATA) (SEQ ID NO:4) were used as primers for obtaining the 5' part of the gene; oligo-3 (TTCGAGTATGM- GAGTGGCCAGACTTCTTA) (SEQ ID NO:5) and oligo-2 were used for the 3' part of the gene.

In the second step, a 1 to 1 mixture of the purified 5' and 3' products from the first step was used as template; oligo-1 and -2 were used as primers. For each step, 10 to 15 cycles (95° C. 0.5 min; 45° C., 0.5 min; 72° C., 0.5 min) of PCR were performed. The final product was cloned into pUC19 and pMAL-c2x resulting in pEndo(Δβ) and pME(Δβ2), respectively. A recognition sequence for restriction enzyme Msc I was generated at the deletion site. For construction of pME (PA/A) from pME(Δβ2), two DNA oligonucleotides,

```
                                        (SEQ ID NO: 6)
oligo-5:   AAAGTGCCTTATGTAATTGCGAGCAATCACAGTTACACT
                                        (SEQ ID NO: 7)
oligo-6:   AGTGTAAGTGTGATTGCACGCAATTACATAAGGCACTTT
```

were annealed, then inserted into the Msc I site of pME(Δβ2). pME(ΔPA) was constructed as pME(PA/A), except for using two different oligonucleotides,

```
                                        (SEQ ID NO: 8)
oligo-7:  AAAGTGCCTTATGTAATTAGCAATCACACTTACACT
and
                                        (SEQ ID NO: 9)
oligo-8:  AGTGTAAGTGTGATTGCTAATTACATAAGGCACTTT.
```

Preparation of Substrates for Heteroduplex Analysis

For construction of pAAT, pACT, pAGT and pATT from pEndo(Δβ2), two oligonucleotide mixtures were:

oligomix-9: AAAGTGCCTTATGTAAATTCCCANTAATCACACTTACACT (SEQ ID NO:10); and oligomix-10: AGTGTAAGTGTGATTANTGGGAATTTACATAAGGCACTTT (SEQ ID NO:11) were annealed, then inserted in the Msc I site of pEndo(Δβ2). The desired individual clones were verified by DNA sequencing.

DNA sequencing was performed on Applied Biosystems, Inc.'s automated DNA sequencers (3100) using Big Dye labeled dye-terminator chemistry (Applied Biosystems, Inc., Foster City, Calif.). The cloned DNA and the DNA used as templates for preparing substrates by PCR were verified by sequencing.

Preparation of Heteroduplex Substrates

For preparation of hybrid substrates by melt-anneal treatment, two purified PCR products described above were mixed in annealing buffer (20 mM Tris. 7.6, 50 mM NaCl) at a 1:1 ratio. The mixture was incubated at 95° C. for 5 minutes followed by incubating at 65° C. for 1 hour, then gradually cooled down to room temperature. For preparation of heteroduplexes by annealing purified single-strand DNA, a positive strand and a negative strand were mixed at 1 to 1 ratio in annealing buffer, then subjected to melt-anneal treatment.

Gene Expression and Protein Purification

Expression and purification of gene products using the MBP fusion and expression system were carried out as described previously (Sambrook, J. and Russell, D. W. (2001) *Molecular Cloning: a Laboratory Manual*, pub. Cold Spring Harbor Laboratory, Cold Spring Harbor, N.Y. (2001); Riggs, P. *Current Protocol in Molecular Biology*, ed. Ausubel, F. A. et al. 16.6.1-16.6.14, pub. Green Associates/Wiley Interscience, New York (1994)). Modifications to the standard protocol and preparation of non-fusion enzyme were described previously (Guan, C., et al. *J. Biol. Chem.* 19:1732-1737 (1996)). The purified enzyme, either the native enzyme or its MBP fusion form, was stored in 50% glycerol at −20° C.

Protein Analysis-Protein concentration was determined by the Bio-Rad Protein Assay using bovine serum albumin as a standard. Molecular weight and purity determinations were carried out by SDS-PAGE analysis and MALDI-ToF mass spectrometry using Applied Biosytems Inc.'s Voyager DE (Applied Biosystems Inc., Foster City, Calif.). N-terminal protein sequence analysis was performed on a Procise 494 Protein/Peptide Sequencer (Applied Biosystems Inc., Foster City, Calif.).

To assay resolvase activity, 1 μg of the cruciform-containing plasmid pUC(AT) in 20 μl of buffer (20 mM Tris, pH 7.6, 50 mM NaCl, 2 mM DDT) with 2 mM $MgCl_2$ or 2 mM $MnCl_2$ was incubated with variable amounts of purified enzyme at 37° C. for 30 minutes. The digests were then analyzed by agarose gel-electrophoresis. Quantitative analysis of DNA or protein bands on the gel was performed on a Bio-Rad Phosphoimage autodensitometer.

Results: Preparation and Overexpression of T7 Endonuclease Mutants

The T7 Endo I gene was obtained by PCR using genomic DNA isolated from T7 phage as a template. The gene was cloned as a 480-base pair (bp) EcoRI-HindIII fragment on plasmid pUC19, named pEndo I, with the orientation of the cloned gene opposed to the lac promoter on the vector. This EcoRI-HindIII fragment should be transferable from pEndo I into the EcoRI-HindIII site of pMAL-c2x plasmid to form an MBP-Endo I in-frame gene fusion. The first attempt to construct the MBP-Endo I fusion in the pMAL system was unsuccessful. The ligation mixture yielded no colonies upon transformation of the host cells, even though multiple copies of the lacIq gene were present in the host. Anticipating that this failure might result from toxic expression even in uninduced cells, a variant pMal vector (pMalC2x-NEB) was constructed with the more-tightly regulated T7 promoter instead (Studier et al. *Meth. Enzymol.* 185:60-89 (1990)). Using this vector, the construct was obtained. In a T7-promoter expression host such as ER2566 or TD-1, 2 to 5 μg of ME could be purified routinely from 1 liter of induced culture.

To generate mutations in the β-bridge while minimizing PCR errors, we constructed an inactive recipient ME fusion vector with the region of interest deleted, to which synthetic oligonucleotides could be added back. Briefly, the DNA encoding the second p sheet (β2), from residue 40 to 53, was removed from pEndo I by two-step PCR, and replaced by an MscI site. The resulting plasmid was named pEndo(Δβ2). The mutated gene Endo(Δβ2) was transferred as an EcoR I-Hind III fragment into the EcoR I-Hind III site of pMAL-c2x to produce plasmid pME(Δβ2). This plasmid was stable in the *E. coli* host TB1 or ER2566. Other mutants were generated by inserting short synthetic double-stranded DNA into the MscI site of pME(Δβ2). The MBP-Endo I mutants were named as follows: ME(ΔPA), where the two residues P46 and A47 located at the 5-bridge center were removed; ME(PA/A) where the dipeptide PA was replaced by the single residue A. The dipeptide PA was also replaced by other single amino acids, dipeptides, tripeptides or tetrapeptides to generate different variants such as ME(PA/G), ME(PA/AA), ME(PA/PGA) and ME(PA/PAPA) and so on. In mutation ME(Abdg), all 6 residues (44-49) that form the bridge were removed.

Figure 1:
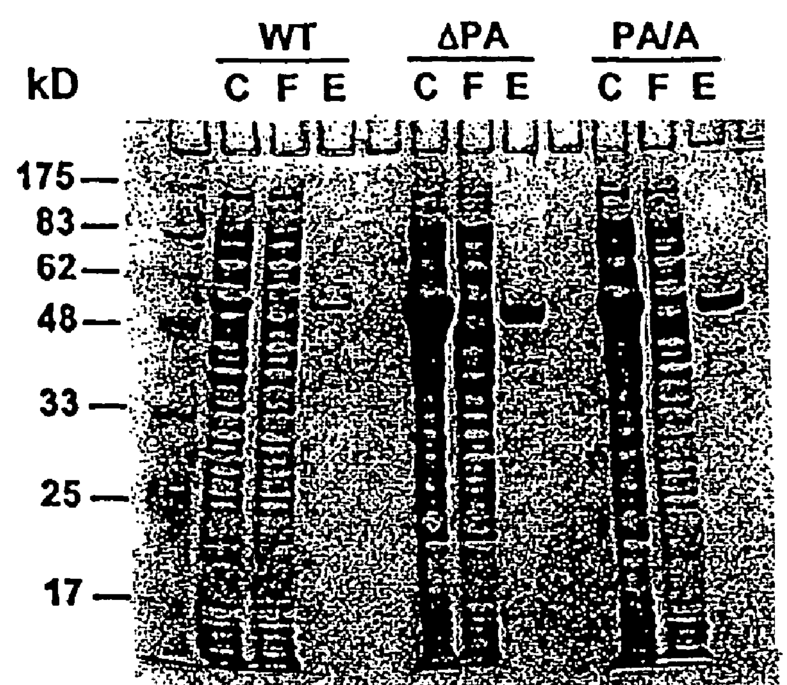
FIG. 1 shows an SDS-PAGE analysis of expression and purification of unmodified MBP-T7 Endo I (ME) protein fusion.

The severe cellular toxicity of T7 EndoI was significantly reduced in many of these mutants, since the mutant genes could be maintained in pMALc-2-x vectors without causing severe host growth defects. In contrast to the wild-type ME, large amounts of MBP-fused mutant proteins were produced after induction. 30-50 mg/L of fusion protein was routinely obtained following a single step of amylose affinity chromatography (FIG. 1).

The purified wild-type ME fusion was as active as the enzyme from which the MBP part had been removed using Factor Xa cleavage, judged by activity titration using pUC (AT) (see Materials and Methods above and discussion below), and taking the molecular weight of fusion protein into account. Since the MBP-Endo I fusion was fully active, the experiments in this study were carried out using the purified fusion proteins.

Example 2

Characterization of Two Deletion Mutants ME(PA/A) and ME(ΔPA)

1. Cleavage of Cruciform Structure DNA

A cruciform structure stabilized on a negatively supercoiled plasmid is structurally similar to a four-way junction of DNA. T7 Endo I resolves both DNA structures with high efficiency (Parkinson, M. J. and Lilley, D. M. J. *J. Mol. Biol.* 270:169-178 (1997)). To compare the enzymatic activities among different T7 Endo I mutants, we defined specific activity using cleavage of a cruciform-containing-plasmid, PUC (AT) as a substrate. One unit of activity was defined as the amount enzyme that was needed to convert 1 μg of supercoiled pUC(AT) to either the linear form (with both strands cut) or the nicked form (with a single strand cut), in 20 ml of reaction at 37° C. in 30 minutes. We measured the specific activity by enzyme titration assay. The results are presented in FIG. 2.

In $Mg^{2+}$ buffer, the specific activities of ME and ME(PA/A) were about the same, 600 to 800 U/mg (FIG. 2, Panels a1 and B1). When $Mg^{2+}$ buffer was replaced with $Mn^{2+}$ buffer, the activity of ME was reduced by about twenty-fold, to only about 40 U/mg (FIG. 2, panel a2). In contrast, the activity for ME(PA/A) remained about the same (600 to 800 U/mg) in either $Mg^{2+}$ or $Mn^{2+}$ buffer (FIG. 2, panels b1 and b2). The final products with either ME or ME(PA/A) were basically the same, linearized plasmid. Singly-nicked intermediates were not observed, suggesting that cleavage of both strands is concerted. Thus, the deletion of proline relieved the $Mn^{2+}$ inhibition without altering the reaction progress.

In contrast, for ME(ΔPA), a change in reaction progress and in ion-dependence was observed. The overall activity of this enzyme was slightly lower, about 400 U/mg, and remained about the same in either $Mg^{2+}$ or $Mn^{2+}$ buffer (FIG. 2, Panels c1 and c2). However, the products were dramatically different from those produced by wild-type and ME(PA/A): in $Mg^{2+}$ buffer most (≧90%) of the final products were nicked plasmids (single cleavage) and less than 10% were linear products (double cleavage; FIG. 2, Panel c1). For this enzyme but not the others, $Mn^{2+}$ affected the identity of the products, increasing the percentage of doubly-cleaved products to 50% (FIG. 2, Panel c2).

We examined the progress of the reaction both at low and at high enzyme: substrate ratio in $Mg^{2+}$ buffer (FIG. 3). Although ME(ΔPA) could eventually convert the nicked plasmid into linear form after a prolonged incubation, or when high concentrations of enzyme were used (FIG. 3, Panel b), at low enzyme concentration the rate of second-strand cleavage was more than 100 times slower than that of the first one. Reaction conditions in substrate excess (with low concentrations of enzyme, as in FIG. 3, Panel a) require each enzyme molecule to carry out multiple turnovers to complete the first strand cleavage on all substrate molecules. Thus, first and second strand cleavage appear to be two separate reactions for this enzyme.

Restriction digestion analysis on the final products of the resolvase reaction confirmed that ME(PA/A) and ME(ΔPA) cleaved pUC(AT) at the cruciform structure site as did ME. Further shortening of the bridge to yield ME(Δbdg) resulted in very low nicking activity (5-10 U/μg) without any double-stranded cleavage. This residual activity was still specific for the cruciform structure.

These results showed that the two catalytic domains in the active mutants were folded correctly and fully active. We also infer that each domain functions independently as a nicking endonuclease. It was necessary to maintain a proper geometrical relation between the two catalytic centers for the enzyme to effectively resolve cruciform DNA. Genetically changing the relative position of the two centers resulted in alteration of the enzyme efficiency, the metal ion preference, the reaction kinetics and the distribution of final products.

2. Non-Specific Endonuclease Activity

Non-specific endonuclease activity of T7 Endo I was observed when high concentrations of enzyme were used. To compare the non-specific nuclease activity among T7 Endo I variants, 1 μg of lambda phage DNA was incubated with variable amounts of enzyme in a 20 ml reaction at 37° C. for 30 minutes. The digests were subjected to gel electrophoresis. The results are presented in FIG. 4.

For the wild type enzyme ME, the non-specific nuclease activity was about the same in either $Mg^{2+}$ or $Mn^{2+}$ buffer (FIG. 4, Panel a1 and Panel a2). This contrasts with the 20-fold ion effect with the specific substrate (see above). Mutations also selectively affected the nonspecific nuclease activity: both mutants ME(PA/A) and ME(ΔPA), showed 20 and 50 times lower non-specific nuclease activity in $Mg^{2+}$ buffer than did ME (FIG. 4, Panels b1 and c1), whereas on the specific substrate there was little reduction in specific activity. $Mn^{2+}$ spared the non-specific nuclease activity of both mutants: nonspecific degradation was achieved at similar or lower enzyme concentrations as observed with ME (FIG. 4, Panels b2 and b2).

Adding $Mg^{2+}$ to the reaction mixture containing $Mn^{2+}$ competitively inhibited the elevated non-specific nuclease activity of ME(PA/A) and ME(ΔPA). Addition of 10 to 20 mM of $Mg^{2+}$ to the 2 mM $Mn^{2+}$ buffer eliminated more than 90% of the non-specific nuclease activity of these enzymes.

Shotgun cloning and sequence analysis of lambda DNA fragments produced by digestion with ME or ME(PA/A) indicated that the enzyme cleaved linear DNA randomly (FIG. 15).

3. Cleavage of Nicked DNA Duplex

We showed above that ME(ΔPA) cleaves DNA at a nick site, eventually converting the nicked intermediate of pUC (AT) to the linear form (FIG. 3, Panel b). To determine whether T7 Endo I could cleave at any nick or only during the progress of a resolution reaction, we made a linear nicked substrate with no cruciform character. Plasmid pNB I (New England Biolabs, Inc., Beverly, Mass.), which contains a single site for the site-specific nicking enzyme N.BstNBI, was digested with the nicking enzyme first, then digested with BsaHI, The resulting product was a 2.5-kb linear DNA molecule with a nick about 600 bp from one end of the molecule. The same protocol without N.BstNBI nicking yielded an un-nicked control substrate. These substrates were then incubated with ME in $Mg^{2+}$ buffer and fragments were resolved on an agarose gel. The nicked substrate yielded the expected 0.6-kb and 1.9-kb DNA fragments in addition to the original 2.5-kb DNA (FIG. 5), while the control yielded only the 2.5-kb substrate DNA. This indicates that T7 Endo I recognizes the presence of a nick in the duplex and cleaves the molecule at or near that site.

Cleavage opposite or approximately opposite a nick is a novel activity, so we investigated the properties of the mutants described above on this new substrate, and again compared the ability of $Mg^{2+}$ or $Mn^{2+}$ to support the reaction. The results are presented in FIG. 6.

In contrast to cruciform resolution, where $Mn^{2+}$ inhibited the wild-type enzyme, the wild-type ME showed equivalent activity at the nick in either $Mg^{2+}$ or $Mn^{2+}$ buffer (FIG. 6, Panels a1 and a2). This suggests that it is the first-strand cleavage of the cruciform that is inhibited by $Mn^{2+}$ for this enzyme. For ME(ΔPA), the activity in $Mg^{2+}$ buffer was undetectable (FIG. 6, Panel c1), while in $Mn^{2+}$ the activity was significantly increased (FIG. 6, Panel c2). This behavior is compatible with its activity on the cruciform substrate, in that $Mg^{2+}$ supported activity on the cruciform resulted primarily in nicked products, while $Mn^{2+}$ resulted in double strand cleavage. This suggests that the enzyme was unable to efficiently complete the resolution reaction by cleaving opposite or approximately opposite to the first nick in $Mg^{2+}$, but that $Mn^{2+}$ supported cleavage opposite or approximately opposite the nick, as seen here.

In the presence of $Mn^{2+}$, ME(PA/A) was a more active enzyme than its wild-type counterpart for nick site cleavage. Indeed, additional products are obtained, not seen with the wild-type where the products corresponded to the increased general non-specific activity observed with this enzyme above. In the present experiment, the amount of enzyme is much less (20 ng) than that used to obtain extensive non-specific activity (400 ng).

FIG. 7 illustrates our approach to determining the location of cleavage of this nick site activity. Briefly, plasmid pNB1 was first treated with nicking enzyme N.BstNB I, then cleaved with ME or ME(PA/A) in $Mn^{2+}$ buffer. The linear plasmids were identified and purified from the agarose gel. After the ends were polished to create flush ends with T4 DNA polymerase plus dNTP, a 300 bp flush-ended Stu I-SnaB I fragment isolated from plasmid Litmus 28 and containing the multiple cloning site and primer binding sites for sequencing was ligated to these products. The recombinant plasmids were isolated from individual transformants and sequenced using the two primers selected from oligonucleotides S12050 and S12051 (NEB, Beverly, Mass.), reading outward from the center of the MCS inserts. The results showed that the endonuclease introduced a single cut, in the continuous strand, displaced 5' from the nick by 3 or 4 bp. These two positions were found with about an equal frequency (data not shown). The sequencing data also showed that under the conditions of the experiment, the enzyme did not cleave the short single-stranded overhangs at sticky ends generated during the reaction, since the duplication created by the fill-in reaction was intact.

4. Cleavage of DNA Heteroduplex with Single-Base Mismatches

To test the ability of T7 Endo I and its mutants to cleave DNA at single-base mismatch sites, we made use of mutated pEndo I genes created during the mutagenesis project. Four individual pEndo I derivatives, named pMT, pACT, pAGT and pATT were constructed (see experimental procedures). The only difference among them was that there was a single base variation at the same position of the gene. Using the 4 individual clones as templates 4 PCR products, about 480 bp long, named pcrAAT, pcrACT, pcrAGT and pcrATT, were obtained. Single-base mismatch heteroduplex molecules could be obtained by mixing any two of the 4 PCR products followed by melt-anneal treatment (Babon, J. J., et al. *Molecular Biotechnology,* 23:73-81 (2003)). 6 hybrid mixture substrates, named hmAAT×ACT, hmAAT×AGT, hmAAT×ATT, hmACT×AGT, hmACT×ATT and hmAGT×ATT, were prepared. Each hybrid mixture was expected to contain two different heteroduplexes besides the two original homoduplexes. For example, hmAAT×ACT contained both A/G and C/T single-base mismatch heteroduplexes besides the original pcrAAT and pcrACT. The mismatch site was about 150 bp away from one end of the molecule. The maximum content of heteroduplexes in an individual hybrid mixture was 50%. Two different hybrid mixtures may contain the same kind of base mismatch, but the sequences flanking the mismatch site are different.

The 6 hybrid mixtures were incubated with ME, ME(PA/A) and ME(ΔPA), respectively, in either $Mg^{2+}$ or $Mn^{2+}$ buffer. The digests were subjected to agarose gel electrophoresis (FIG. 8). The results showed that in all cases, ME digested the heteroduplex to create 150-bp and 330-bp from the original 480-bp one. In the control directly using pcrMT, ACT, AGT or ATT as substrates, only the original 480-bp DNA band could be identified (FIG. 8, panels a1 and a2). These indicated that ME cut at least one of the two heteroduplexes present in each of 6 hybrid mixtures. The cleavage efficiency on these substrates with ME was about the same in either $Mg^{2+}$ or $Mn^{2+}$ buffer. However, in $Mg^{2+}$ buffer the cleavage with ME(PA/A) or ME(ΔPA) was almost undetectable (FIG. 8, Panels b1 and c1). The cleavage efficiency for ME(PA/A) or ME(ΔPA) was significantly increased by replacing $Mg^{2+}$ with $Mn^{2+}$ in the reaction (FIG. 8, Panels b2 and c2). In the presence of $Mn^{2+}$, ME(PA/A) was at least as active as ME was for cleavage of single-base mismatched DNA in hybrid mixture substrates. ME(ΔPA) was a less active enzyme, even in $Mn^{2+}$ buffer.

In order to assess the cleavage efficiency of the enzyme with each kind of single-base mismatch, we prepared heteroduplex substrates, each of which contained only one of the possible mismatches (FIG. 9, Panel A). Briefly, 8 single-strand DNA molecules, about 480 base long, named ssAAT(+), ssMT(−), ssACT(+), ssACT(−) and so on were generated, using lambda exonuclease to selectively digest one strand of the relevant PCR product Annealing each one of the positive strands with each one of the negative strands could produce 16 duplex DNA molecules, 12 of them single-base mismatch heteroduplexes and 4 homoduplex molecules (FIG. 9, Panel B). The base mismatch site was about 150 bp away from one of the ends of the molecules. Some heteroduplexes may contain the same kind of mismatches, but the sequences around the mismatches are different.

The 16 DNA duplexes prepared above were incubated with ME and ME(PA/A) in $Mn^{2+}$ buffer respectively. The digests were resolved on agarose gels (FIG. 10). The results showed that the 4 regular DNA duplex molecules generated by annealing two corresponding positive and negative strands were not specifically cleaved by either ME (FIG. 10, Panel A) or ME(PA/A) (FIG. 10, Panel B). Both enzymes could effectively cleave heteroduplexes at the single-base mismatch sites where at least one of the mismatched bases was cytosine. Neither enzyme cleaved DNA at a G/G mismatch site very efficiently. The most profound difference between the two enzymes was that ME(PA/A) had much higher activity at A/A and T/T mismatches than did ME. In general, ME(PA/A) in the presence of $Mn^{2+}$ was a more efficient enzyme than its wild type counterpart when cleaving DNA at single-base mismatch sites. To determine the cutting pattern by the enzyme at single-base mismatch sites, we performed an experiment as illustrated in FIG. 11, Panel a. Briefly, plasmids pMT, pACT, pAGT and pATT were linearized by digestion with HindIII. The four linear plasmids were mixed and subjected to melting-anneal treatment. The annealed plasmid mixture was treated with T4 ligase plus ATP to produce relaxed circular molecules. The majority (up to 75%) of the recircularized plasmids should contain a single-base mismatch site that is sensitive to cleavage by T7 Endo I. The ligation mixture was digested with ME(PA/A) in $Mn^{2+}$ buffer followed by treatment with T4 DNA polymerase plus dNTP to blunt the ends, then subjected to agarose electrophoresis. The DNA band representing the full-length linear plasmids was isolated from the gel (FIG. 11, Panel b). The purified linears were treated with T4 ligase and transformed into an *E. coli* host TB1. Plasmids were isolated from individual transformants sequence across the ligation junction using a primer located 150 bp away from the original mismatch site. The results showed that ME(PA/A) cleaved both strands of DNA 5' to, and 1 to 3 bp away from, the mismatched base, generating 3 to 7 (many of them 4 to 6) bp long sticky ends, as judged by the length of the duplication generated at the mismatch site.

What is claimed is:

1. A composition, comprising:

a variant T7 Endo I polypeptide having endonuclease activity, and comprising an amino acid sequence that differs from the amino acid sequence of its parent T7 Endo I polypeptide solely by one or more mutations in a β-bridge corresponding to amino acids 44-49 of SEQ ID NO: 12.

2. The composition according to claim 1, wherein the endonuclease activity comprises greater DNA cleavage activity of the variant T7 Endo I polypeptide in a manganese-containing buffer compared with the DNA cleavage activity of the parent T7 Endo I polypeptide in the manganese-containing buffer.

3. The composition according to claim 2, wherein the DNA cleavage activity is selected from the group consisting of: cleavage of a cruciform DNA; nicking opposite a preexisting nick site; nicking next to a mismatch in the DNA resulting in double strand cleavage; and non-specific nuclease activity.

4. The composition according to claim 1, wherein the endonuclease activity comprises reduced DNA cleavage activity of the variant T7 Endo I polypeptide in a magnesium-containing buffer compared with the DNA cleavage activity of the parent T7 Endo I polypeptide in the magnesium-containing buffer.

5. The composition according to claim 4, wherein the DNA cleavage activity is selected from the group consisting of: nicking opposite a preexisting nick site; nicking next to a mismatch in the DNA resulting in double strand cleavage; and non-specific nuclease activity.

6. The composition according to claim 1, wherein the one or more mutations is a substitution or a deletion at a site corresponding to a Pro-Ala (PA) dipeptide in the β-bridge corresponding to amino acids 44-49 of SEQ ID NO:12.

7. The composition according to claim 6, wherein the substitution is a single amino acid substitution, a dipeptide substitution, a tripeptide substitution, or a tetrapeptide substitution; or wherein the deletion is a deletion of the PA dipeptide, deletion of Pro, or deletion of Ala.

8. The composition according to claim 7, wherein the PA dipeptide is substituted with an Ala (A), a Lys (K), a Gly (G), an Asp (D), a Pro (P), an Ala-Ala (AA) dipeptide, an Ala-Gly-Ala (AGA) tripeptide, or a Pro-Ala-Pro-Ala (PAPA) peptide.

9. A kit comprising the composition of claim 6.

10. A method of forming a shotgun cloning library, comprising:

(a) incubating the composition of claim 1 with a DNA to form non-sequence specific cleavage fragments of the DNA that are ligatable; the ligatable DNA being capable of insertion into a vector for cloning into a vector for cloning in a host cell; and (b) forming the shotgun cloning library.

11. A method for mapping nicks in a duplex DNA, comprising:

(a) incubating the composition of claim 1 with the duplex DNA in a manganese-containing buffer;

(b) permitting nicking to occur across from a pre-existing nick site to form fragments of the duplex DNA with single strand overhangs; and (c) mapping the nicks in the DNA.

* * * * *

SEQUENCE LISTING

```
<160> NUMBER OF SEQ ID NOS: 23

<210> SEQ ID NO 1
<211> LENGTH: 450
<212> TYPE: DNA
<213> ORGANISM: unknown
<220> FEATURE:
<223> OTHER INFORMATION: enterobacteria phage T7

<400> SEQUENCE: 1

atggcaggtt acggcgctaa aggaatccga aaggttggag cgtttcgctc tggcctagag      60

gacaaggttt caaagcagtt ggaatcaaaa ggtattaaat tcgagtatga agagtggaaa     120

gtgccttatg taattccggc gagcaatcac acttacactc cagacttctt acttccaaac     180

ggtatattcg ttgagacaaa gggtctgtgg gaaagcgatg atagaaagaa gcacttatta     240

attagggagc agcaccccga gctagacatc cgtattgtct tctcaagctc acgtactaag     300

ttatacaaag gttctccaac gtcttatgga gagttctgcg aaaagcatgg tattaagttc     360

gctgataaac tgatacctgc tgagtggata aaggaaccca agaaggaggt cccctttgat     420

agattaaaaa ggaaaggagg aaagaaataa                                      450


<210> SEQ ID NO 2
<211> LENGTH: 27
<212> TYPE: DNA
<213> ORGANISM: artificial
<220> FEATURE:
<223> OTHER INFORMATION: primer

<400> SEQUENCE: 2

cccgaattca tggcaggtta cggcgct                                           27


<210> SEQ ID NO 3
<211> LENGTH: 27
<212> TYPE: DNA
<213> ORGANISM: artificial
<220> FEATURE:
<223> OTHER INFORMATION: primer

<400> SEQUENCE: 3

cccccaagct tatttctttc ctccttt                                           27


<210> SEQ ID NO 4
<211> LENGTH: 30
<212> TYPE: DNA
<213> ORGANISM: unknown
<220> FEATURE:
<223> OTHER INFORMATION: primer

<400> SEQUENCE: 4
```

-continued tggaagtaag aagtctggcc actcttcata 30

<210> SEQ ID NO 5
<211> LENGTH: 30
<212> TYPE: DNA
<213> ORGANISM: artificial
<220> FEATURE:
<223> OTHER INFORMATION: primer

<400> SEQUENCE: 5
ttcgagtatg aagagtggcc agacttctta 30

<210> SEQ ID NO 6
<211> LENGTH: 39
<212> TYPE: DNA
<213> ORGANISM: unknown
<220> FEATURE:
<223> OTHER INFORMATION: oligonucleotide

<400> SEQUENCE: 6
aaagtgcctt atgtaattgc gagcaatcac acttacact 39

<210> SEQ ID NO 7
<211> LENGTH: 39
<212> TYPE: DNA
<213> ORGANISM: unknown
<220> FEATURE:
<223> OTHER INFORMATION: oligonucleotide

<400> SEQUENCE: 7
agtgtaagtg tgattgcacg caattacata aggcacttt 39

<210> SEQ ID NO 8
<211> LENGTH: 36
<212> TYPE: DNA
<213> ORGANISM: unknown
<220> FEATURE:
<223> OTHER INFORMATION: oligonucleotide

<400> SEQUENCE: 8
aaagtgcctt atgtaattag caatcacact tacact 36

<210> SEQ ID NO 9
<211> LENGTH: 36
<212> TYPE: DNA
<213> ORGANISM: unknown
<220> FEATURE:
<223> OTHER INFORMATION: oligonucleotide

<400> SEQUENCE: 9
agtgtaagtg tgattgctaa ttacataagg cacttt 36

<210> SEQ ID NO 10
<211> LENGTH: 40
<212> TYPE: DNA
<213> ORGANISM: unknown
<220> FEATURE:
<223> OTHER INFORMATION: oligonucleotide mixture
<220> FEATURE:
<221> NAME/KEY: misc_feature
<222> LOCATION: (24)..(24)
<223> OTHER INFORMATION: n is a, c, g, or t

<400> SEQUENCE: 10
aaagtgcctt atgtaaattc ccantaatca cacttacact 40

-continued

```
<210> SEQ ID NO 11
<211> LENGTH: 40
<212> TYPE: DNA
<213> ORGANISM: unknown
<220> FEATURE:
<223> OTHER INFORMATION: oligonucleotide mixture
<220> FEATURE:
<221> NAME/KEY: misc_feature
<222> LOCATION: (17)..(17)
<223> OTHER INFORMATION: n is a, c, g, or t

<400> SEQUENCE: 11

agtgtaagtg tgattantgg gaatttacat aaggcacttt                          40


<210> SEQ ID NO 12
<211> LENGTH: 149
<212> TYPE: PRT
<213> ORGANISM: unknown
<220> FEATURE:
<223> OTHER INFORMATION: enterobacteria phage T7

<400> SEQUENCE: 12

Met Ala Gly Tyr Gly Ala Lys Gly Ile Arg Lys Val Gly Ala Phe Arg
1               5                   10                  15

Ser Gly Leu Glu Asp Lys Val Ser Lys Gln Leu Glu Ser Lys Gly Ile
            20                  25                  30

Lys Phe Glu Tyr Glu Glu Trp Lys Val Pro Tyr Val Ile Pro Ala Ser
        35                  40                  45

Asn His Thr Tyr Thr Pro Asp Phe Leu Leu Pro Asn Gly Ile Phe Val
    50                  55                  60

Glu Thr Lys Gly Leu Trp Glu Ser Asp Asp Arg Lys Lys His Leu Leu
65                  70                  75                  80

Ile Arg Glu Gln His Pro Glu Leu Asp Ile Arg Ile Val Phe Ser Ser
                85                  90                  95

Ser Arg Thr Lys Leu Tyr Lys Gly Ser Pro Thr Ser Tyr Gly Glu Phe
            100                 105                 110

Cys Glu Lys His Gly Ile Lys Phe Ala Asp Lys Leu Ile Pro Ala Glu
        115                 120                 125

Trp Ile Lys Glu Pro Lys Lys Glu Val Pro Phe Asp Arg Leu Lys Arg
    130                 135                 140

Lys Gly Gly Lys Lys
145


<210> SEQ ID NO 13
<211> LENGTH: 151
<212> TYPE: PRT
<213> ORGANISM: unknown
<220> FEATURE:
<223> OTHER INFORMATION: yersinia pestis phage phiA1122

<400> SEQUENCE: 13

Met Ala Gly Thr Tyr Ala Ala Arg Gly Ile Arg Lys Val Gly Thr Phe
1               5                   10                  15

Arg Ser Gly Leu Glu Asp Lys Val Ser Lys Gln Leu Glu Gly Lys Gly
            20                  25                  30

Ile Lys Phe Asp Tyr Glu Leu Trp Lys Ile Pro Tyr Val Val Pro Ala
        35                  40                  45

Ser Asn His Val Tyr Thr Pro Asp Phe Leu Leu Pro Asn Gly Ile Phe
    50                  55                  60

Ile Glu Thr Lys Gly Leu Trp Glu Ser Asp Asp Arg Lys Lys His Leu
65                  70                  75                  80
```

```
Leu Ile Arg Glu Gln Phe Pro Glu Leu Asp Ile Arg Leu Val Phe Ser
                85                  90                  95

Ser Ser Arg Thr Lys Leu Tyr Lys Gly Ser Pro Thr Ser Tyr Gly Glu
            100                 105                 110

Trp Cys Glu Lys His Gly Ile Leu Phe Ala Asp Lys Leu Ile Pro Val
        115                 120                 125

Glu Trp Leu Lys Glu Pro Lys Lys Glu Val Pro Phe Asp Arg Leu Lys
    130                 135                 140

Gln Ala Lys Gly Gly Lys Lys
145                 150


<210> SEQ ID NO 14
<211> LENGTH: 153
<212> TYPE: PRT
<213> ORGANISM: unknown
<220> FEATURE:
<223> OTHER INFORMATION: bacteriophage phiYe03-12

<400> SEQUENCE: 14

Met Ala Gly Ala Tyr Ala Ala Arg Gly Val Arg Lys Val Gly Ala Phe
1               5                   10                  15

Arg Ser Gly Leu Glu Asp Lys Val Ser Lys Gln Leu Glu Ser Lys Gly
            20                  25                  30

Ile Lys Phe Asp Tyr Glu Leu Trp Arg Ile Pro Tyr Val Ile Pro Ala
        35                  40                  45

Ser Asp His Leu Tyr Thr Pro Asp Phe Leu Leu Pro Asn Gly Ile Phe
    50                  55                  60

Ile Glu Thr Lys Gly Leu Trp Asp Ser Asp Asp Arg Lys Lys His Leu
65                  70                  75                  80

Leu Ile Arg Glu Gln His Pro Glu Leu Asp Ile Arg Leu Val Phe Ser
                85                  90                  95

Ser Ser Arg Ser Lys Leu Tyr Lys Gly Ser Pro Thr Ser Tyr Ala Glu
            100                 105                 110

Trp Cys Glu Lys His Gly Ile Leu Phe Ala Asp Lys Leu Ile Pro Val
        115                 120                 125

Glu Trp Leu Lys Glu Pro Lys Lys Glu Val Pro Phe Asp Lys Phe Lys
    130                 135                 140

Thr Lys Lys Gly Val Lys Lys Asn Gly
145                 150


<210> SEQ ID NO 15
<211> LENGTH: 152
<212> TYPE: PRT
<213> ORGANISM: Bacteriophage T3

<400> SEQUENCE: 15

Met Ala Gly Ala Tyr Ala Ala Arg Cys Thr Gln Gly Arg Ala Phe Arg
1               5                   10                  15

Ser Gly Leu Glu Asp Lys Val Ser Lys Gln Leu Glu Ser Lys Gly Ile
            20                  25                  30

Lys Phe Asp Tyr Glu Leu Trp Arg Ile Pro Tyr Val Ile Pro Glu Ser
        35                  40                  45

Asp His Leu Tyr Thr Pro Asp Phe Leu Leu Pro Asn Gly Ile Phe Ile
    50                  55                  60

Glu Thr Lys Gly Leu Trp Asp Ser Asp Asp Arg Lys Lys His Leu Leu
65                  70                  75                  80
```

-continued

```
Ile Arg Glu Gln His Pro Glu Leu Asp Ile Arg Leu Val Phe Ser Ser
                85                  90                  95

Ser Arg Ser Lys Leu Tyr Lys Gly Ser Pro Thr Ser Tyr Gly Glu Trp
            100                 105                 110

Cys Glu Lys His Gly Ile Leu Phe Ala Asp Lys Leu Ile Pro Val Ala
        115                 120                 125

Gly Val Lys Glu Pro Lys Lys Glu Val Pro Phe Asp Lys Phe Lys Thr
    130                 135                 140

Lys Lys Gly Val Lys Lys Asn Gly
145                 150


<210> SEQ ID NO 16
<211> LENGTH: 147
<212> TYPE: PRT
<213> ORGANISM: unknown
<220> FEATURE:
<223> OTHER INFORMATION: pseudomonas phage gh-1

<400> SEQUENCE: 16

Met Ala Tyr Ala Gly Pro Lys Gly Ala Arg Thr Gly Ala Phe Arg Ser
1               5                   10                  15

Gly Leu Glu Asp Arg Asn Ala Lys His Met Asp Lys Leu Gly Val Lys
            20                  25                  30

Tyr Asp Phe Glu Arg Phe His Ile Asn Tyr Val Val Pro Ala Arg Asp
        35                  40                  45

Ala Lys Tyr Thr Pro Asp Phe Val Leu Ala Asn Gly Ile Ile Ile Glu
    50                  55                  60

Thr Lys Gly Ile Trp Glu Val Asp Asp Arg Lys Lys His Leu Leu Ile
65                  70                  75                  80

Arg Glu Gln Tyr Pro Asp Leu Asp Ile Arg Leu Val Phe Ser Asn Ser
                85                  90                  95

Asn Ser Lys Ile Tyr Lys Gly Ser Pro Thr Ser Tyr Ala Asp Phe Cys
            100                 105                 110

Thr Lys His Gly Ile Gln Phe Ala Asp Lys Leu Val Pro Arg Asp Trp
        115                 120                 125

Leu Lys Glu Ala Arg Lys Glu Ile Pro Gln Gly Val Leu Val Pro Lys
    130                 135                 140

Lys Gly Gly
145


<210> SEQ ID NO 17
<211> LENGTH: 141
<212> TYPE: PRT
<213> ORGANISM: unknown
<220> FEATURE:
<223> OTHER INFORMATION: pseudomonas putida KT2440

<400> SEQUENCE: 17

Met Gly Leu Lys Tyr Gly Phe Arg Ser Gly Leu Glu Glu Arg Ala Ala
1               5                   10                  15

Asp Gln Leu Thr Ala Val Gly Met Gly Phe Thr Phe Glu Ser Leu Val
            20                  25                  30

Val Pro Tyr Thr Arg Pro Ala Lys Val His Lys Tyr Thr Pro Asp Phe
        35                  40                  45

Ala Leu Ala Asn Gly Ile Ile Val Glu Thr Lys Gly Arg Phe Leu Thr
    50                  55                  60

Glu Asp Arg Gln Lys Gln Leu Leu Val Lys Ala Gln His Pro Glu Leu
65                  70                  75                  80
```

-continued

```
Asp Val Arg Phe Val Phe Ser Asn Ser Lys Thr Lys Ile Asn Lys Arg
                85                  90                  95

Ser Thr Thr Thr Tyr Ala Asp Trp Cys Ser Lys Asn Gly Phe Gln Tyr
            100                 105                 110

Ala Asp Lys Leu Val Pro His Ala Trp Leu Asn Glu Pro Val Asn Glu
        115                 120                 125

Ala Ser Leu Ser Ile Ile Lys Gly Leu Ser Lys Glu Lys
    130                 135                 140
```

<210> SEQ ID NO 18
<211> LENGTH: 134
<212> TYPE: PRT
<213> ORGANISM: unknown
<220> FEATURE:
<223> OTHER INFORMATION: roseophage SI01

<400> SEQUENCE: 18

```
Met Leu Asn Ser Lys Ser Ser Thr Arg Lys Arg Ala Leu Lys Ala Gly
1               5                   10                  15

Tyr Arg Ser Gly Leu Glu Glu Gln Thr Ala Lys Asp Leu Lys Lys Arg
            20                  25                  30

Lys Val Leu Phe Thr Tyr Glu Glu Thr Lys Ile Lys Trp Leu Asp Ser
        35                  40                  45

Lys Val Arg Thr Tyr Thr Pro Asp Phe Val Leu Pro Asn Gly Val Ile
    50                  55                  60

Ile Glu Thr Lys Gly Arg Phe Val Ala Ala Asp Arg Arg Lys His Leu
65                  70                  75                  80

Glu Ile Gln Lys Gln Phe Gly Thr Leu Tyr Asp Ile Arg Phe Val Phe
                85                  90                  95

Thr Asn Ser Lys Ala Lys Leu Tyr Lys Gly Ala Lys Ser Ser Tyr Ala
            100                 105                 110

Asp Trp Cys Asn Lys His Gly Phe Leu Tyr Ala Asp Lys Thr Ile Pro
        115                 120                 125

Glu Asp Trp Leu Asn Glu
    130
```

<210> SEQ ID NO 19
<211> LENGTH: 14
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (9)..(9)
<223> OTHER INFORMATION: mismatch

<400> SEQUENCE: 19
aattcccaat aatc 14

<210> SEQ ID NO 20
<211> LENGTH: 20
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (9)..(9)
<223> OTHER INFORMATION: mismatch
<220> FEATURE:
<221> NAME/KEY: misc_feature

```
<222> LOCATION: (15)..(15)
<223> OTHER INFORMATION: mismatch

<400> SEQUENCE: 20

aattcccagt accaataatc                                              20


<210> SEQ ID NO 21
<211> LENGTH: 18
<212> TYPE: DNA
<213> ORGANISM: unknown
<220> FEATURE:
<223> OTHER INFORMATION: synthetic
<220> FEATURE:
<221> NAME/KEY: misc_feature
<222> LOCATION: (9)..(9)
<223> OTHER INFORMATION: mismatch
<220> FEATURE:
<221> NAME/KEY: misc_feature
<222> LOCATION: (13)..(13)
<223> OTHER INFORMATION: mismatch

<400> SEQUENCE: 21

aattcccagt caataatc                                                18


<210> SEQ ID NO 22
<211> LENGTH: 149
<212> TYPE: PRT
<213> ORGANISM: unknown
<220> FEATURE:
<223> OTHER INFORMATION: enterobacteria phage T7

<400> SEQUENCE: 22

Met Ala Gly Tyr Ser Ala Lys Gly Ile Arg Lys Val Gly Ala Phe Arg
1               5                   10                  15

Ser Gly Leu Glu Asp Lys Val Ser Lys Gln Leu Glu Ser Lys Gly Ile
            20                  25                  30

Lys Phe Glu Tyr Glu Glu Trp Lys Val Pro Tyr Val Ile Pro Ala Ser
        35                  40                  45

Asn His Thr Tyr Thr Pro Asp Phe Leu Leu Pro Asn Gly Ile Phe Val
    50                  55                  60

Glu Thr Lys Gly Leu Trp Glu Ser Asp Asp Arg Lys Lys His Leu Leu
65                  70                  75                  80

Ile Arg Lys Gln His Pro Glu Leu Asp Ile Arg Ile Val Phe Ser Ser
                85                  90                  95

Ser Arg Thr Lys Leu Tyr Lys Gly Ser Pro Thr Ser Tyr Gly Glu Phe
            100                 105                 110

Cys Glu Lys His Gly Ile Lys Phe Ala Asp Lys Leu Ile Pro Ala Glu
        115                 120                 125

Trp Ile Lys Glu Pro Lys Lys Glu Val Pro Phe Asp Arg Leu Lys Arg
    130                 135                 140

Lys Gly Gly Lys Lys
145


<210> SEQ ID NO 23
<211> LENGTH: 149
<212> TYPE: PRT
<213> ORGANISM: unknown
<220> FEATURE:
<223> OTHER INFORMATION: enterobacteria phage T7

<400> SEQUENCE: 23

Met Val Gly Tyr Gly Val Lys Gly Ile Arg Lys Val Gly Ala Phe Arg
1               5                   10                  15
```

-continued

```
Ser Gly Leu Glu Asp Lys Val Ser Lys Gln Leu Glu Ser Lys Gly Ile
            20                  25                  30

Lys Phe Glu Tyr Glu Glu Trp Lys Val Pro Tyr Val Ile Pro Ala Ser
        35                  40                  45

Asn His Thr Tyr Thr Pro Asp Phe Leu Leu Pro Asn Gly Ile Phe Val
    50                  55                  60

Glu Thr Lys Gly Leu Trp Glu Ser Asp Asp Arg Lys Lys His Leu Leu
65                  70                  75                  80

Ile Arg Glu Gln His Pro Glu Leu Asp Ile Arg Ile Val Phe Ser Ser
                85                  90                  95

Ser Arg Thr Lys Leu Tyr Lys Gly Ser Pro Thr Ser Tyr Gly Glu Phe
            100                 105                 110

Cys Glu Lys His Gly Ile Lys Phe Ala Asp Lys Leu Ile Pro Ala Glu
        115                 120                 125

Trp Ile Lys Glu Pro Lys Lys Glu Val Ser Phe Asp Arg Leu Lys Arg
    130                 135                 140

Lys Gly Gly Lys Lys
145
```